United States Patent
David et al.

(10) Patent No.: US 8,442,615 B2
(45) Date of Patent: May 14, 2013

(54) PHYSIOLOGICAL MEASURING SYSTEM COMPRISING A GARMENT IN THE FORM OF A SLEEVE OR GLOVE AND SENSING APPARATUS INCORPORATED IN THE GARMENT

(75) Inventors: Daniel David, Rananna (IL); Irving Levy, Rishon Lezion (IL)

(73) Assignee: Commwell Research and Development, Ltd., Kfar Saba (IL)

( * ) Notice: Subject to any disclaimer, the term of this patent is extended or adjusted under 35 U.S.C. 154(b) by 211 days.

(21) Appl. No.: 12/898,430

(22) Filed: Oct. 5, 2010

(65) Prior Publication Data
US 2011/0224530 A1     Sep. 15, 2011

Related U.S. Application Data

(60) Continuation-in-part of application No. 11/742,904, filed on May 1, 2007, now abandoned, which is a division of application No. 10/899,484, filed on Jul. 26, 2004, now abandoned, which is a continuation-in-part of application No. 10/324,303, filed on Dec. 20, 2002, now Pat. No. 6,842,722, which is a continuation of application No. 10/117,250, filed on Apr. 5, 2002, now Pat. No. 6,516,289, which is a continuation of application No. 09/359,340, filed on Jul. 21, 1999, now abandoned.

(51) Int. Cl.
*A61B 5/0408* (2006.01)

(52) U.S. Cl.
USPC .......................................... 600/388; 600/393

(58) Field of Classification Search .................. 600/388, 600/393
See application file for complete search history.

(56) References Cited

U.S. PATENT DOCUMENTS

| | | | |
|---|---|---|---|
| 4,572,197 A | 2/1986 | Moore et al. |
| 4,583,547 A | 4/1986 | Granek et al. |
| 4,608,987 A | 9/1986 | Mills |
| 4,747,413 A | 5/1988 | Bloch |
| 4,854,323 A | 8/1989 | Rubin |
| 4,920,969 A | 5/1990 | Suzuki et al. |
| 4,949,729 A | 8/1990 | Haski |
| 5,007,427 A | 4/1991 | Suzuki et al. |
| 5,072,458 A | 12/1991 | Suzuki |

(Continued)

FOREIGN PATENT DOCUMENTS

| | | |
|---|---|---|
| EP | 0760225 A1 | 3/1997 |
| EP | 0846440 A  | 6/1998 |

(Continued)

OTHER PUBLICATIONS

EP 11194367.6—European Search Report, Jan. 23, 2012.

(Continued)

*Primary Examiner* — Lee S Cohen
(74) *Attorney, Agent, or Firm* — Banner & Witcoff, Ltd.

(57) ABSTRACT

A measuring system for measuring electrocardiogram signals comprises a diagnostic garment with ECG electrodes that may assume the form of a sleeve or glove. A disposable version of the glove can be inflated. By using an inflatable glove, the contour of the body is automatically matched by the contour of the glove. Samples from the ECG electrodes positioned on a diagnostic garment are compensated so that the samples better approximate samples from EEG electrodes that are positioned at classical locations. Also, samples from ECG electrodes are compensated to reduce signal noise resulting from positioning the ECG electrodes on the diagnostic garment.

6 Claims, 20 Drawing Sheets

U.S. PATENT DOCUMENTS

| | | | |
|---|---|---|---|
| 5,210,706 A | 5/1993 | Nishiyama | |
| 5,224,479 A | 7/1993 | Seknie | |
| 5,353,793 A | 10/1994 | Bornn | |
| 5,431,170 A | 7/1995 | Mathews | |
| 5,465,727 A | 11/1995 | Reinhold, Jr. | |
| 5,511,546 A | 4/1996 | Hon | |
| 5,685,303 A | 11/1997 | Rollman et al. | |
| 5,704,364 A | 1/1998 | Saltzstein | |
| 5,715,548 A | 2/1998 | Weismiller et al. | |
| 5,724,025 A | 3/1998 | Tavori | |
| 5,730,140 A | 3/1998 | Fitch | |
| 5,748,367 A | 5/1998 | Lücke et al. | |
| 5,855,550 A | 1/1999 | Lai et al. | |
| 5,885,231 A | 3/1999 | Cramer et al. | |
| 5,987,982 A | 11/1999 | Wenman et al. | |
| 6,009,764 A | 1/2000 | Fukunaga | |
| 6,047,203 A | 4/2000 | Sackner et al. | |
| 6,223,606 B1 | 5/2001 | Burke et al. | |
| 6,224,548 B1 | 5/2001 | Gopinathan et al. | |
| 6,248,064 B1 | 6/2001 | Gopinathan et al. | |
| 6,516,289 B2 | 2/2003 | David | |
| 6,842,722 B2 | 1/2005 | David | |
| 6,884,218 B2 | 4/2005 | Olson | |
| 7,112,175 B2 | 9/2006 | Gopinathan et al. | |
| 7,396,331 B2 | 7/2008 | Mack et al. | |
| 7,785,257 B2 | 8/2010 | Mack et al. | |
| 2003/0083587 A1 | 5/2003 | Ferek-Petric | |
| 2004/0019261 A1 | 1/2004 | Gopinathan et al. | |
| 2004/0082870 A1 | 4/2004 | Rudy | |
| 2008/0077020 A1 | 3/2008 | Young et al. | |
| 2010/0210921 A1 | 8/2010 | Park et al. | |

FOREIGN PATENT DOCUMENTS

| | | |
|---|---|---|
| JP | 200014652 A | 6/1998 |
| WO | 9302616 A | 2/1993 |
| WO | 9960919 A1 | 12/1999 |

OTHER PUBLICATIONS

Francis D B et al.: "Compensating the vcg for variations in electrode positions", Proceedings of the 20th Annual Conference on Engineering in Medicine and Biology IEEE New York, NY, USA 1967.

Sunemark M et al.: Serial VCG/ECG analysis using neural networks:, Computers and Biomedical Research, Academic Press, London, GB vol. 31, Jan. 1, 1998, pp. 59-69.

Notice of Allowance from U.S. Appl. No. 13/092,570, dated Mar. 8, 2012.

PHYSIOLOGICAL MEASURING SYSTEM COMPRISING A GARMENT IN THE FORM OF A SLEEVE OR GLOVE AND SENSING APPARATUS INCORPORATED IN THE GARMENT

CROSS REFERENCE TO RELATED APPLICATIONS

This is a continuation-in-part utility application based upon, incorporating by reference and claiming priority to application Ser. No. 11/742,904 (now abandoned), filed May 1, 2007 entitled "Physiological Measuring System Comprising a Garment in the Form of a Sleeve or Glove and Sensing Apparatus Incorporated in the Garment" which is a divisional of application Ser. No. 10/899,484 (now abandoned), filed Jul. 26, 2004 entitled "Physiological Measuring System Comprising a Garment in the Form of a Sleeve or Glove and Sensing Apparatus Incorporated in the Garment", which is a continuation-in-part of application Ser. No. 10/324,303, filed on Dec. 20, 2002 entitled "Physiological Measuring System Comprising a Garment in the Form of a Sleeve or Glove and Sensing Apparatus Incorporated in the Garment" and granted as U.S. Pat. No. 6,842,722 on Jan. 11, 2005, application Ser. No. 10/324,303 is a continuation application of application Ser. No. 10/117,250 filed Apr. 5, 2002 entitled "Physiological Measuring System Comprising a Garment and Sensing Apparatus Incorporated in the Garment" and granted as U.S. Pat. No. 6,516,289 on Feb. 4, 2003, application Ser. No. 10/117,250 is a continuation of application Ser. No. 09/359,340 (expressly abandoned), filed Jul. 21, 1999 entitled "Physiological Measuring System Comprising a Garment in the Form of a Sleeve or Glove and Sensing Apparatus Incorporated in the Garment", application Ser. Nos. 11/742,904; 10/899,484; 10/324,303; 10/117,250, and 09/359,340 are incorporated herewith by reference and for which priority is claimed.

BACKGROUND OF THE INVENTION

The field of the invention is in the design of devices for the acquisition, storage and transmission of multiple physiological parameters from human subjects to be monitored in hospitals, clinics, doctor's offices as well as in remote locations (home environment, work place, recreational activity, etc.) or unnatural environments (under-water, outer space, etc.).

The conventional acquisition of a human electrocardiogram (ECG) requires the recording of the time dependent fluctuations in the cardiac electrical activation from 12 different angles on the human torso (6 in the frontal plane and 6 in the horizontal plane) the so-called 12 lead ECG. Classically, this procedure involves the placement on the human body of at least 10 electrodes at various predefined anatomical locations.

Deviation from the predefined, worldwide, conventional localization of these electrodes may result in the acquisition of false data, possibly leading to misinterpretation and misdiagnosis. Even in the hospital or clinic environment, the correct and stable placement of the ECG electrodes, specifically the "chest leads" or "V leads" is often problematic, unless one applies six adhesive electrodes on the patient's chest. This is an impractical method in many circumstances due mainly to financial and patient inconvenience considerations. This problem is amplified in the attempts to record a full diagnostic 12 lead ECG in a remote location since the correct positioning of the electrodes by the examinee himself or by available laymen bystanders (family members, friends, etc.) is usually difficult and unreliable and therefore impractical.

To overcome this problem and to allow for the accurate acquisition of a 12 lead ECG in the ambulatory environment, various devices were conceived. Such devices include various forms of vests, girdles, adhesive and non-adhesive patches and other devices with incorporated electrodes allowing for the placement of the ECG electrodes on the patient's chest. However, most of these devices are cumbersome to use and have therefore not been universally accepted. Moreover, these devices do not lend themselves to the integration of other sensors and instrumentation for the simultaneous acquisition of other important physiological data (blood pressure, Sp02, etc.), such data being very useful for the purpose of ambulatory telemedical follow-up of patients in their own environment (home, workplace, recreational activity, etc).

SUMMARY OF THE INVENTION

The invention proposes to integrate a multitude of sensors and measuring devices in a diagnostic garment in the form of a glove or sleeve for repeated continuous and simultaneous assessment of various physiological data such as ECG, non-invasive blood pressure (NIBP), blood oxygen saturation (Sp02), skin resistance, motion analysis, an electronic stethoscope, etc. An important advantage of the glove or sleeve is that it provides accurate, repeatable and conventional placement or localization of the ECG electrodes (specifically for the recording of the chest or V leads) by positioning the left arm of patient in a natural and very comfortable manner on the chest. Moreover, the glove or sleeve provides a means for simultaneous recording, storage and transmission of a multitude of other physiological data without the need for difficult manipulations. Furthermore, the incorporation of various measuring tools or instruments into one device, i.e. glove or sleeve, allows for the reciprocal calibration and easy acquisition of important, integrated, physiological data, a feature presently almost unavailable in the ambulatory environment (e.g. beat to beat NIBP changes, integration of: heart rate, blood pressure, skin resistance and other parameters for the assessment of autonomic balance, etc.).

With one aspect of the invention, samples from the ECG electrodes positioned on a diagnostic garment (e.g., a glove or sleeve) are compensated so that the samples better approximate samples from EEG electrodes that are positioned at classical locations. With an embodiment of the invention, a first mean QRS vector is selected from a first plurality of mean QRS vectors associated with standard electrodes and second mean QRS vector is selected from a second plurality of mean QRS vectors associated with the diagnostic garment.

With another aspect of the invention, samples from ECG electrodes are compensated to reduce signal noise that may result by positioning the ECG electrodes on the diagnostic garment.

With another aspect of the invention, a disposable version of the glove can be inflated. By using an inflatable glove, the contour of the body is automatically matched by the contour of the glove. The matching contours will allow for a close fit between the electrodes and the skin.

A further aspect of the invention relates to the inflatable glove which is capable of assuming the contour of the body and which is also disposable. The contoured glove incorporates electrodes and thereby may enable appropriate positioning of ECG electrodes.

Another aspect of the invention is the design of the inflatable glove which may be incorporated with a sling or a similar device such as a sleeve or holder will be separable from and capable of appropriately positioning and holding the inflatable glove.

These and other objects, advantages, features and aspects of the invention will be set forth in the detailed description which follows.

BRIEF DESCRIPTION OF THE DRAWING

In the detailed description which follows, reference will be made to the drawing comprised of the following figures.

DESCRIPTION OF THE PREFERRED EMBODIMENTS

Figure 3:
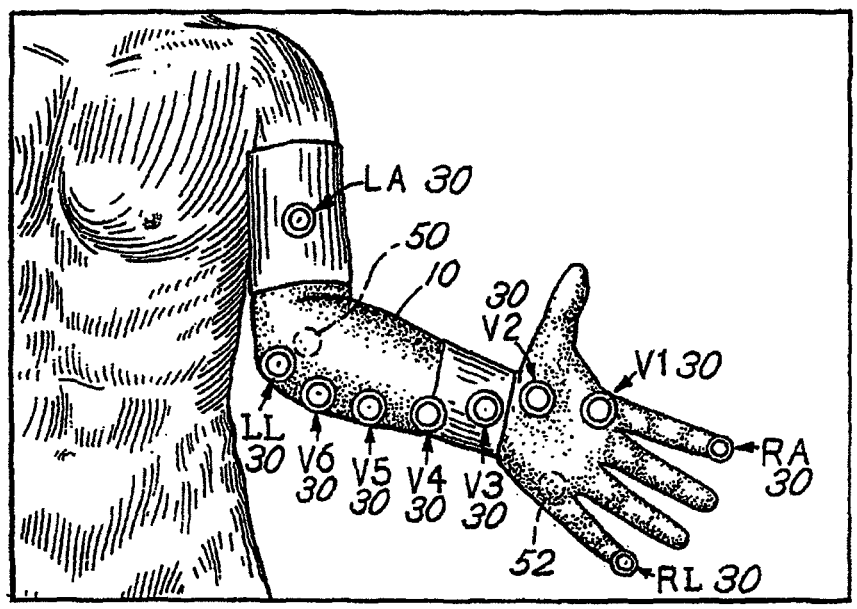
FIG. 3 depicts the ventral aspect of the glove or sleeve device illustrating the suggested location of the various ECG electrodes to permit easy placement of the ECG electrodes at predefined locations on a patient's body for recording a diagnostic 12 Lead ECG. Furthermore, two small microphones are depicted on the ventral side of the glove to be connected with the electronic stethoscope located in the central control unit.
Figure 4:
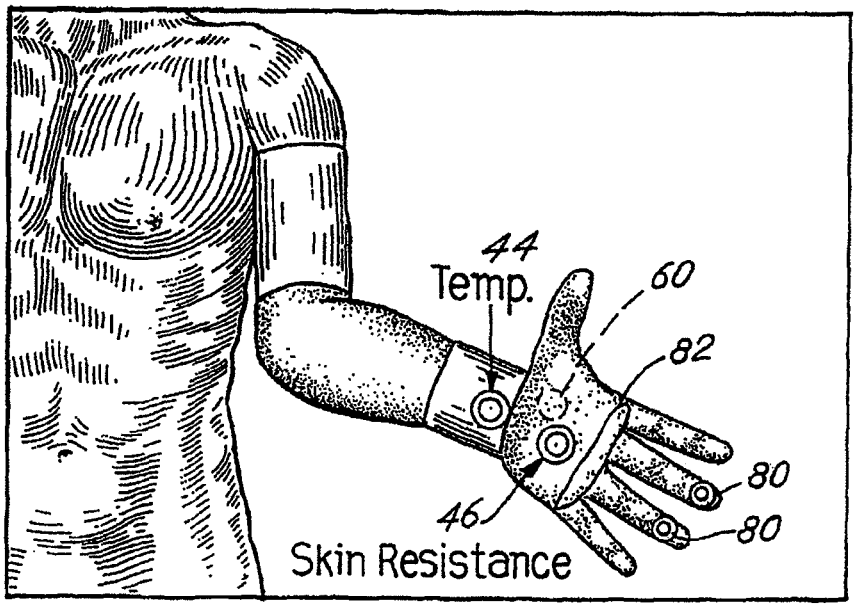
FIG. 4 depicts the ventral aspect of the glove or sleeve device depicting mainly the suggested location of other possible sensors for the determination of other physiological data such as temperature, skin resistance, etc.
Figure 5:
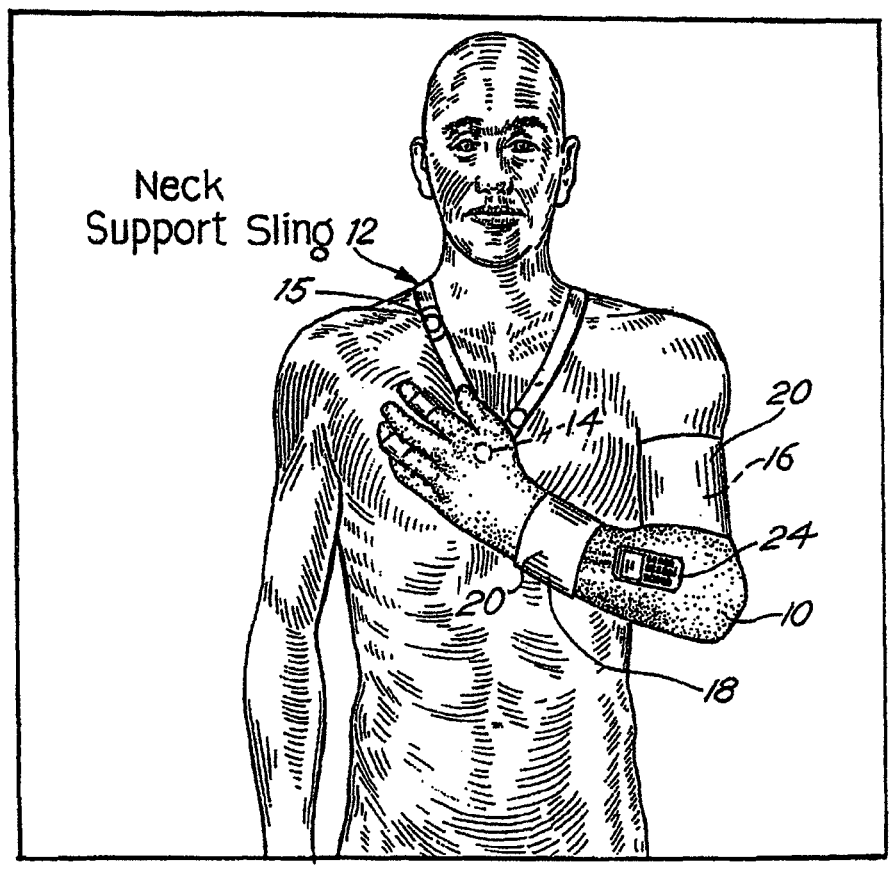
FIG. 5 depicts the advised positioning of the patient's left arm with the glove or sleeve device on the patient's chest to ensure proper localization of the 12 lead ECG electrodes for accurate and reproducible 12 lead ECG recordings, as well as the proper positioning of an electronic stethoscope. This arm position, aided by a neck sling which may also contain an additional ECG electrode, is natural and comfortable and therefore allows for prolonged, stable and continuous monitoring of all desired physiological parameters.

As depicted in FIGS. 2-5, the garment of the invention is preferably in the form of a glove or sleeve or combined glove and sleeve 10 and is fabricated from flexible material such as a nylon fabric that can fit snugly, without causing discomfort, on a human hand, forearm and arm. The glove or sleeve 10 is sized to fit or conform to patient arm size and shape. A neck sling 12 is attached to the glove or sleeve 10. The neck sling 12 is also adaptable and adjustable to the individual patient to ensure accurate positioning or elevation of the left arm on the chest of the patient for the proper placement of the ECG electrodes. Moreover, the neck sling 12 may include an additional ECG electrode 14 (FIG. 5).

Two blood-pressure cuffs 16, 18 are incorporated in the glove or sleeve 10. One cuff 16 is positioned on the arm in the conventional blood-pressure measuring location, the second cuff 18 is placed on the forearm. Special restraining straps 20 mounted on the outside of the glove are wrapped around the blood-pressure cuffs 16, 18 to allow proper restrainment during cuff inflation. The blood-pressure cuffs 16, 18 are connected by a flexible tube 22, 23 to a central control unit or device 24 for inflation, deflation, and measurement of blood pressure by conventional methodology and used in the automatic determination of NIBP.

At least ten ECG electrodes 30 are attached to the glove or sleeve 10 as depicted in FIG. 3. All of the ECG electrodes 30 except the LA electrode face the patient's chest whereas the LA electrode 30 is in contact with the skin of the left upper arm. The RA electrode 30 or its equivalent is placed either on the index finger of the glove 10 in the neck sling 12, or in another suitable position. All of the electrodes 30 are wire connected to the ECG recording device located in the central control unit 24 retained in the sleeve 10.

The ECG electrodes 30 included the following features:
(a) An automatic electrolyte solution application device. In the course of the recording of a conventional ECG, it is the routine to manually apply an electrolyte solution or cream to the contact surface between the skin and the recording electrodes to cause a reduction of skin resistance and to improve the conduction of the electrical current between the skin and the according electrode. In the described glove or sleeve 10, each electrode 30 includes means for automatic injection of an electrolyte solution into each electrode 30 prior to the acquisition of the ECG. This is achieved by connection of each electrode to an electrolyte reservoir by means of connecting tubes 32. Prior to the acquisition of the ECG recording, the electrolyte solution will be automatically sprayed into the electrodes 30 by pressure provided by a pump located in the central control unit 24.

(b) A suction device for better electrode-skin contact: The ECG electrodes 30 will be configured as suction electrodes 30 and will be connected via suction tubes 34 to a pump located in the central control unit 24. Once the glove or sleeve 10 is placed on the chest in the proper position, an external signal will activate the pump to create the needed negative pressure and suction to maintain the proper electrode-skin contact. Following the termination of the ECG recording, the negative pressure will be abolished allowing detachment of the electrodes from the patient's chest. The same or separate pumps may be utilized to effect electrolyte application and the creation of electrode suction.

A conventional IR SpO2 measuring device 36 is incorporated in the glove or sleeve 10 and placed on one of the glove finger tips 38 to fit the patient's finger. Blood SpO2 is determined using the conventional methods applied for this measurement and the results will be stored in the central control unit 24.

A conventional finger Plethysmographic-measuring device 38 is incorporated in one of the glove fingertips 40 to fit on the patient's finger. An external restraining device 42 ensures continuous snug contact with the finger to provide continuous beat to beat changes in finger blood volume variation. The finger plethysmograph is wire connected to the central control unit 24. The signal is periodically calibrated using the conventional cuff blood pressure measurements thereby allowing for continuous beat to beat blood pressure monitoring.

A thermistor 44 is incorporated in the glove or sleeve 10 and located on the ventral surface of the arm in direct contact with the skin to allow the determination of skin temperature. The thermistor 44 is wire connected to the central control unit 24.

A conventional sensor 46 for the determination of skin resistance is incorporated in the glove or sleeve 10 and wire connected to the central control unit 24.

Two special microphones 50, 52 are attached to the ventral aspect of the glove or sleeve 10, one located over the base of the left lung and the second on one of the fingers for the simultaneous auscultation of both lungs. Furthermore, the finger microphones 50, 52 can also be moved to enable auscultation of the heart and other organs. The microphones 50, 52 will be connected to the central control unit 24 for recording and transmission of the auscultatory findings.

Motion and force assessment devices 60, 80, 82 are incorporated in the glove or sleeve 10 mainly for the early detection of neurological and neuromuscular dysfunction. Sensors 60 assess passive and active functions such as:

(a) Force of muscular contraction (e.g., handgrip, arm flexion and extension, etc.)
(b) Passive pathological arm and finger motion (Parkinsonian tremor, flapping tremor, etc.).
(c) Assessment of active finger, hand or arm motion (rapid hand pronation and supination, rapid finger motion, etc.).

Figure 2:
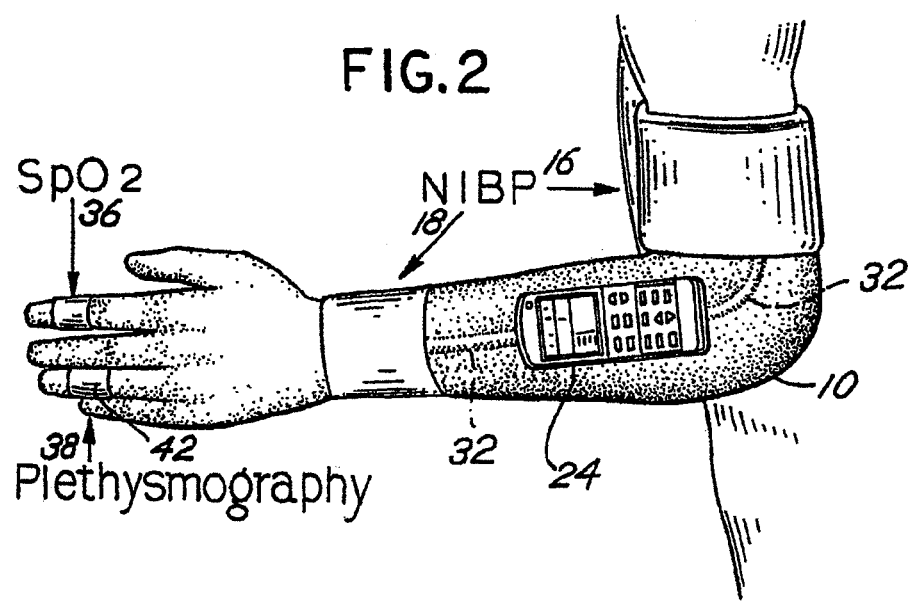
FIG. 2 depicts the central unit that includes all of the control functions for the various devices incorporated in the glove or sleeve device of the invention as well as on-line storage, analog to digital conversion and transmission capabilities of all acquired data; two blood-pressure cuffs (wrist and arm); and Sp02 and plethysmographic sensors (fingers).

The glove or sleeve 10 is equipped with a central control unit 24 attached to the dorsal aspect of the glove or sleeve 10 (FIG. 2). The general function of this unit 24 is the collection, transformation, storage and transmission of all of the physiological data collected from the various devices incorporated in the glove 10. Moreover, the central control unit 24 includes mechanical and other devices such as pumps, injectors, etc., needed for the proper functioning of the incorporated devices as described herein.

Specifically, the central control unit 24 includes the appropriate measuring element for each sensor. The measured data is digitized, stored and upon demand, made available for transmission by RF or IR or any other form of wireless telemetric transmission to a remote surveillance center. Conversely, the central control unit 24 has the ability to receive signals from a remote surveillance center for the activation or deactivation and other control functions of the various measuring devices incorporated in the glove 10.

In review, the glove 10 provides an unobtrusive stable platform for self-application of numerous physiological sensors using a glove and/or sleeve 10 and an optional neck support sling 12 to perform various simultaneous non-invasive on invasive health-care related measurements for use in the home, workplace, recreational, clinic or hospital environment. The invention has the advantage over other methods of sensor applications in that no prior knowledge of proper sensor placement is required and that proper placement of the sensors on the patient is assured. The sensor position is stable and reproducible. The invention improves the repeatability of measurements by insuring that the placement and distances between the various sensors remain constant. Moreover, the interplay between the various sensors can result in the combination of data acquisition integration and analysis adding major sophistication and improvement as compared to the individual use of each measuring devices.

In further review, the glove/sleeve 10 together with the optional neck support sling 12 contains one or more of the following measuring elements:

(a) An optical emitter and detector 36 attached to the index finger of the glove 10 for the purpose of measuring the level of oxygen saturation in the blood, and peripheral pulse (FIG. 2).
(b) A finger plethysmograph device 38 for continuous, beat to beat, noninvasive arterial blood pressure measurement (calibrated by the mean of the arterial blood pressure determinations derived from both the wrist and arm NIBP devices) (FIG. 2).
(c) Inflatable cuff and pressure cuffs or sensor 16, 18 located in various locations on the arm and hand to measure brachial radial or finger blood pressure for periodic (automatic or manual) noninvasive blood pressure measurements (NIBP). These NIBP measuring devices are also used to calibrating the optical system used to measure continuous, beat to beat arterial blood pressure as above mentioned (FIG. 2).
(d) A central control unit 24 for the acquisition and transmission of the various bio-signals derived from the glove sensors. This central control unit 24 which can be activated locally by the patient or remotely by a monitoring center allows for automatic or manual activation of any or all of the sensors. The central control unit 24 provides amongst other: the initial and repeated sensor calibration procedures, activation of a built-in miniature pump for the creation of positive and negative pressures, the reception of commands from the remote control center, analog to digital conversion of measured data and their transmission to the control center as well as any other needed control functions (FIG. 2).
(e) A set of electrodes 30 (V1, V2, RA, RL) placed on the palmar aspect of the glove 10 and/or the neck support sling 12 for the purpose of simultaneous recording of a twelve-lead electrocardiogram (FIG. 3).

(f) A method for automatic administration of an electric conductor solution/cream to the electrodes 30 to reduce skin resistance and improve ECG relating quality.

(g) A method of producing and maintaining a sufficient negative pressure (suction) inside the ECG electrodes 30 to insure proper contact between the ECG electrode and the skin (FIG. 3).

(h) A method of insuring proper contact between the ECG electrodes 30 and the skin by the application of an air cushion or a gel cushion around areas of the glove that are in contact with the skin. The cushion is used to provide a body contour fit (FIG. 3).

(i) A method such as a buckle connection 15 to adjust the sling 12 to ensure that the arm is held at the proper level for accurate placement of the ECG electrodes 30 on the patients body.

(j) A temperature sensor 40 placed in appropriate areas of the glove/sleeve 10 for the purpose of measuring body temperature (FIG. 4).

(k) An electrode or set of electrodes 46 placed in the palm area of the glove for the purpose of measuring skin resistance (FIG. 4).

(l) An electronic stethoscope for the auscultation of lungs, heart and other organs.

(m) Built-in measuring devices 80 in FIG. 4 in the glove fingers for the accurate assessment of tremor and other normal or neurological forms of finger motions.

(n) Built in measuring devices 80 in the glove 10 for the determination of EMG.

(o) Built-in measuring devices 80 in the glove 10 for the determination of nerve conduction.

(p) Built-in measuring device 82 for the determination of muscle force (hand grip, extension, flexion, etc.).

(q) Built-in device 82 for the assessment of rapid/accurate voluntary hand movement.

(r) The advised positioning of the patient's left arm on the chest to ensure proper localization of the 12 lead ECG electrodes of the glove for accurate and reproducible 12 lead ECG recording is shown in FIG. 5. This arm position, aided by the adjustable neck support sling 12, is natural and comfortable and therefore allows for prolonged, stable and continuous monitoring of all available parameters (FIG. 5).

Figure 6:
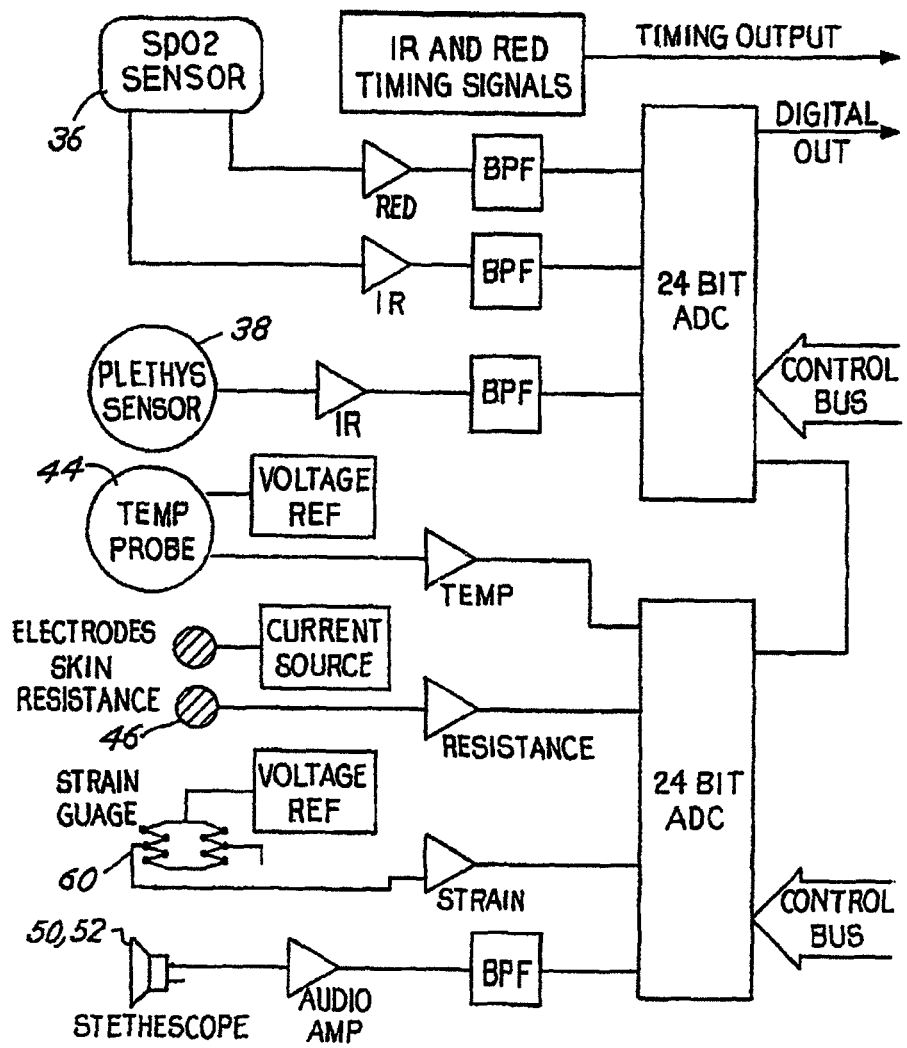
FIG. 6 is a schematic circuit diagram of sensor inputs for the system.

FIGS. 6, 7, 8 and 9 are schematic drawings depicting the basic elements described above. FIG. 6 depicts the various sensors including the SpO2 sensor 36, the plethysmography sensor 38, the temperature sensor 44, skin resistance probes 46, strain gauges 48, and stethoscope sensors 50, 52. As depicted in FIG. 6, each of the inputs in amplified and, if necessary, filtered prior to being converted to a 24 bit analog to digital converter. The output of the analog to digital converter goes via a control ASIC depicted in FIG. 9 to a dual port ram also in FIG. 9 where it is processed and transmitted by a microprocessor and an infrared communications to a stationary unit.

Figure 7:
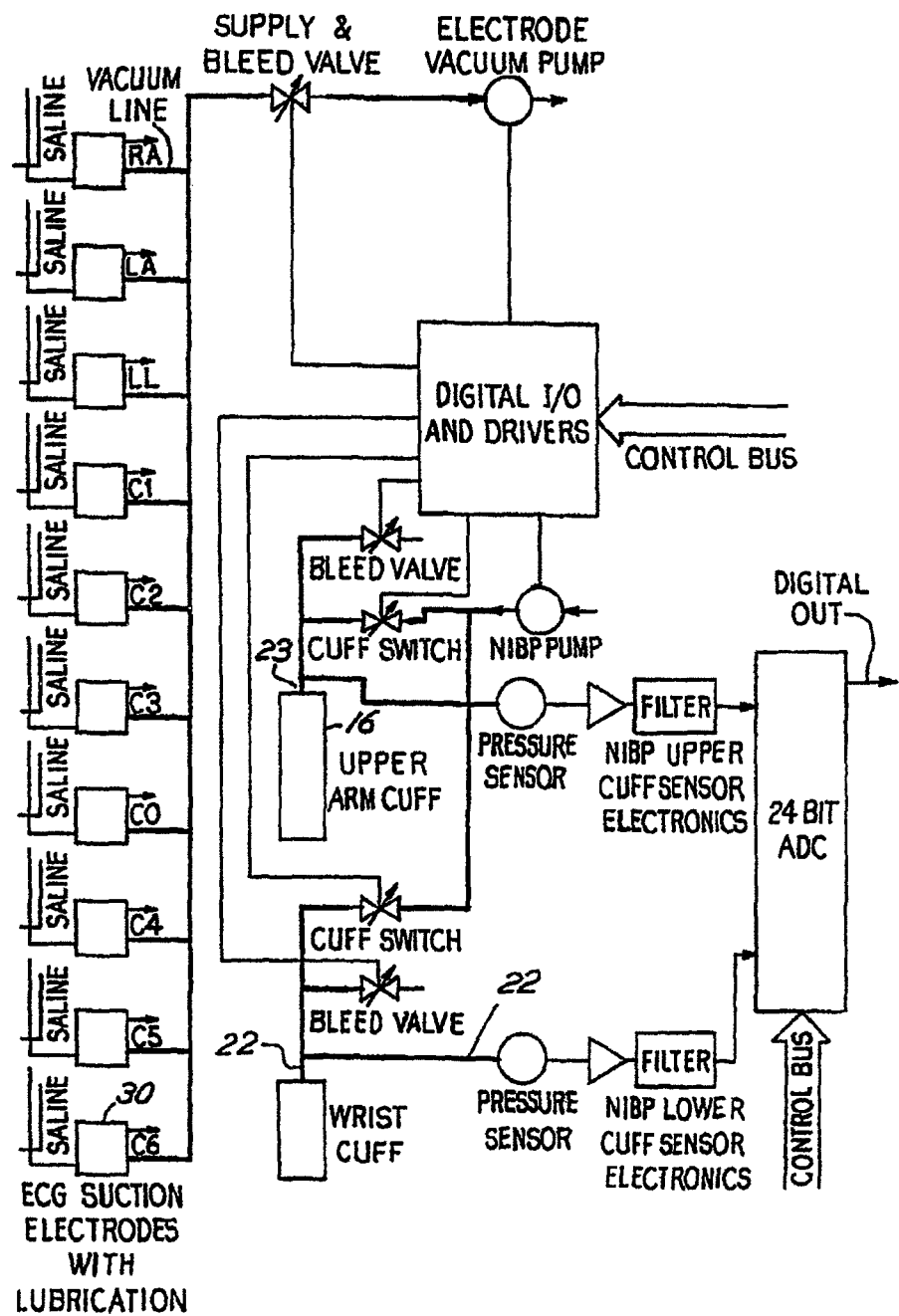
FIG. 7 is a schematic mechanical system diagram of the ECG inputs and blood pressure inputs.

FIG. 7 depicts the various mechanical elements and connections for the ECG electrodes and the blood pressure mechanical and electronic portion of the system. Each ECG electrode comprises a container that holds a saline solution or another lubricant. This solution is drawn into the electrode via a vacuum system. A bleed valve closes the system and then releases the vacuum. The release of the vacuum will then release the lubricant or solution. Digital input output drivers control the vacuum pump and the bleed valve in response to signals that are provided from the ASIC control lines. In the embodiment disclosed, there are two blood pressure cuffs, one associated with the wrist and one with the upper arm. A blood pressure pump (NIBP pump) pumps each cuff. A pressure sensor then measures the pressure in each cuff. The values from the pressure sensor are amplified, filtered and converted to digital values in the 24-bit analog to digital converter. The output of the analog to digital converter also passes through the control ASIC in FIG. 9 to the dual port random access memory unit where it is processed and transmitted by the microprocessor and IR communications, for example, to a stationary unit.

Figure 8:
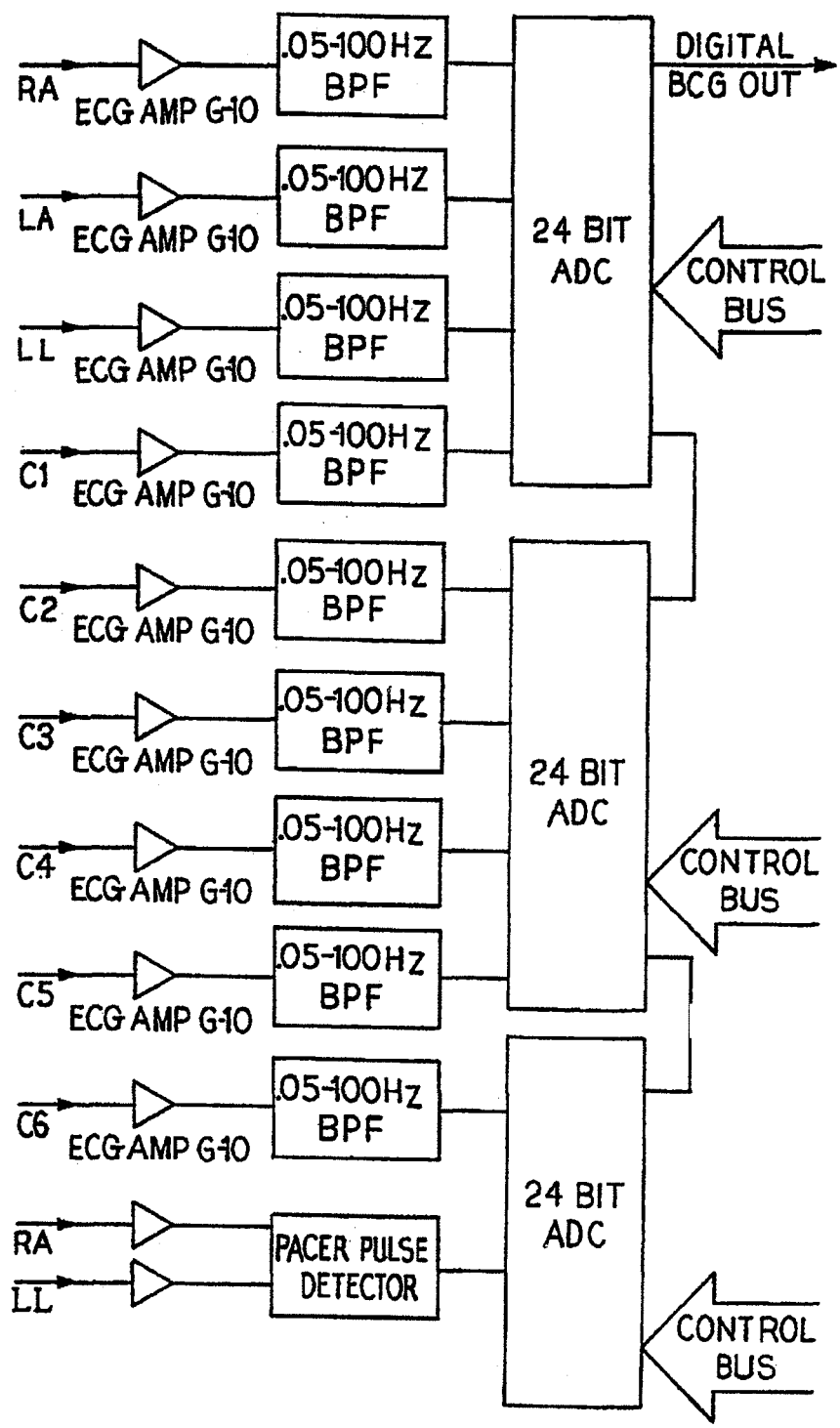
FIG. 8 is a schematic circuit diagram of the input circuitry for the ECG measurements.

FIG. 8 depicts the ECG analog input circuitry. Each electrode input is separately amplified and ban passed filtered prior to conversion by a 24-bit analog to digital converter. The analog to digital converter signal passes through the control ASIC in FIG. 9 to the dual port RAM where it is processed and transmitted again by the microprocessor and IR communications to a stationary unit.

Figure 9:
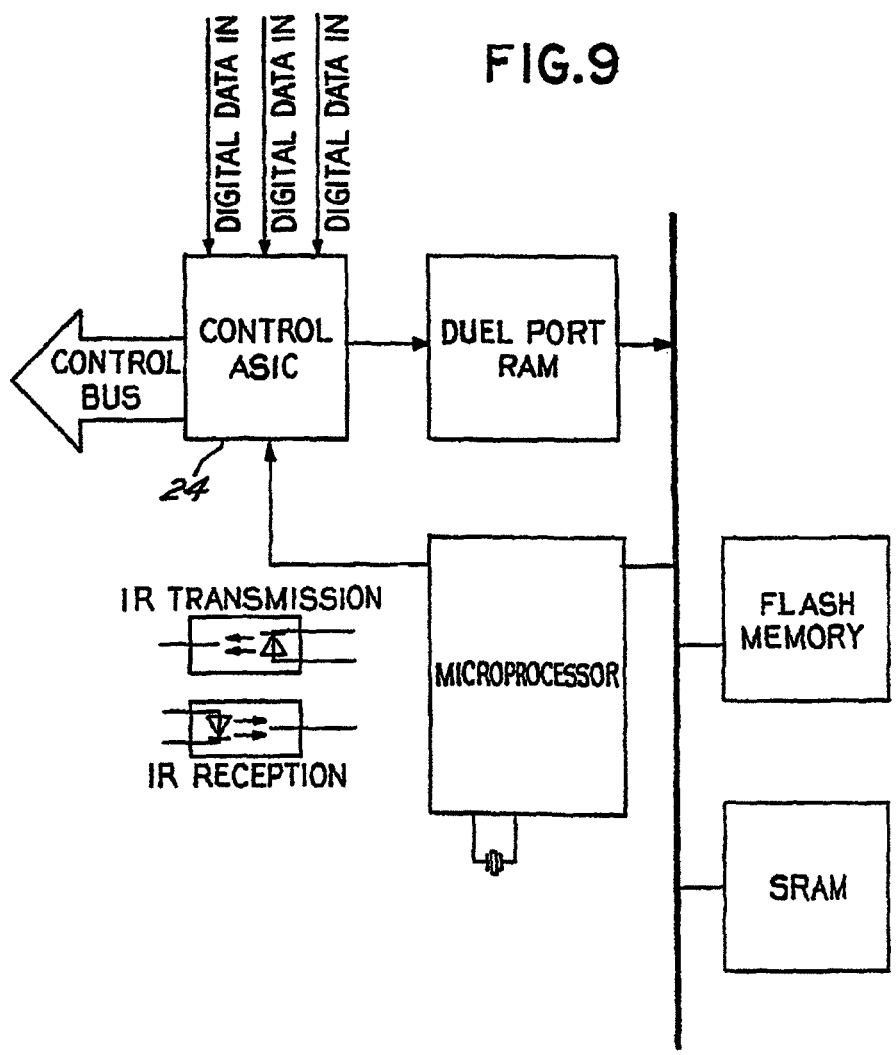
FIG. 9 is a schematic circuit diagram for the overall system.

FIG. 9 depicts the digital circuitry in the system. The circuitry includes the ASIC which has logic for the timing signals and for transmitting or passing the digitized analog signals from the various analog to digital converters to the dual port RAM which sits on the microprocessor. The microprocessor runs the software provided from the flash memory, collects data samples, performs basic analysis, controls the various valves and pumps and sends data to the central data collector via IR communication. The described circuitry is but one way to accomplish the goals and objectives of the use of the glove and/or sleeve of the invention.

Electrode Compensation

Embodiments of the invention enhance a vector representation of the ECG waveforms. As will be discussed, methods and apparatuses provide for adjusting a vector representation of ECG signals to compensate for positioning ECG electrodes on a diagnostic garment (e.g., the glove/sleeve as discussed above) rather than classically positioning the electrodes on a patient's limbs as with standard ECG electrodes. Also, an embodiment of the invention compensates for additional signal noise that may be imposed on the EEG signals resulting from the positioning of the EEG electrodes on the diagnostic garment.

Cardiac activity generates a measurable amount of electric current. The current is recorded through an electrocardiograph and displayed as an EEG waveform, the shape of which is governed by both the magnitude and direction of the current flow. The EEG waveforms may be displayed as vectors whose trajectories also depict the magnitude and direction of the heart's impulses as will be discussed with FIG. 11. The average of these vectors for a particular heart cycle is called the mean QRS vector and is displayed on a vector image as a solid arrow whose length is the average magnitude and whose angle is the average direction.

Figure 10:
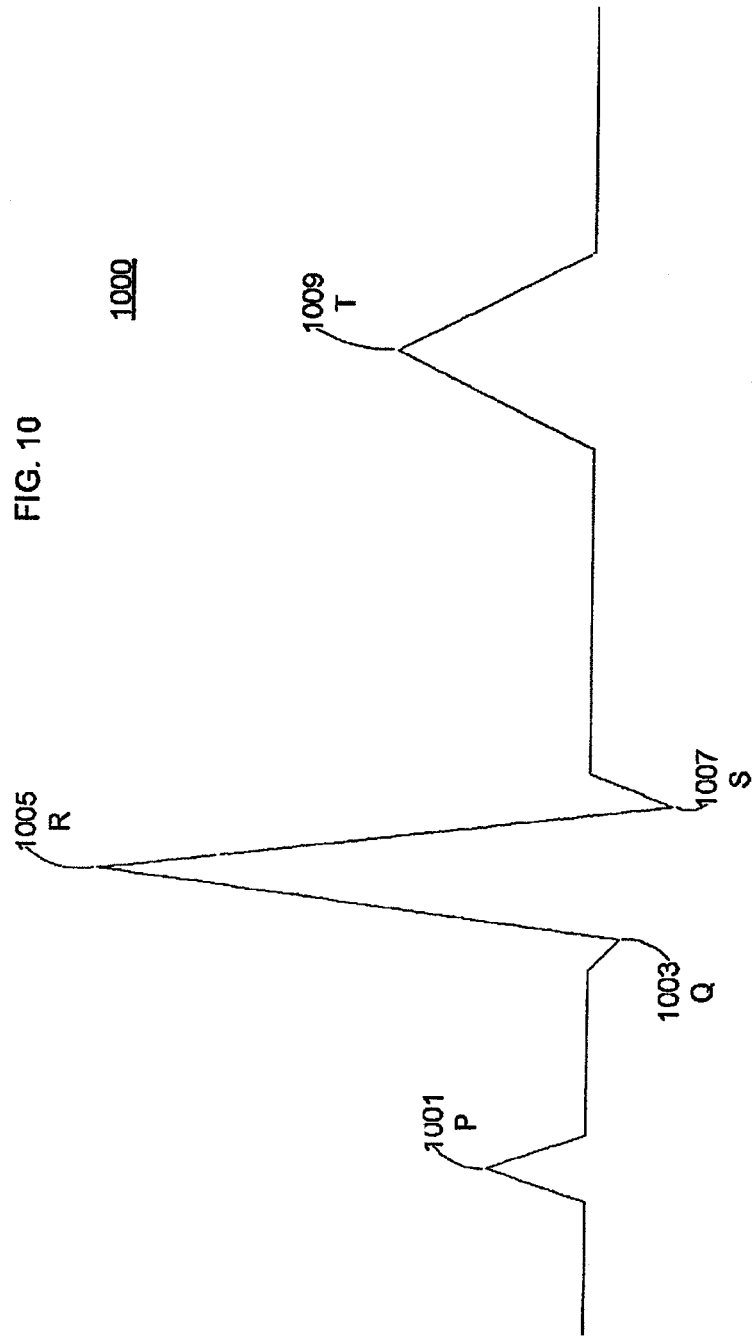
FIG. 10 shows a simplified representation of an exemplary ECG waveform that is obtained from an ECG lead in accordance with an embodiment of the invention.

FIG. 10 shows a simplified representation 1000 of an exemplary ECG waveform that is obtained from an ECG lead in accordance with an embodiment of the invention. In normal sinus rhythm, each P wave 1001 is followed by a QRS complex (comprising Q wave 1003, R wave 1005, and S wave 1007). The QRS complex represents the time it takes for depolarization of the ventricles. Activation of the anteroseptal region of the ventricular myocardium corresponds to the negative Q wave 1003. However, Q wave 1003 is not always present. Activation of the rest of the ventricular muscle from the endocardial surface corresponds to the remainder of the QRS complex. The R wave 1005 is a point when half of the ventricular myocardium has been depolarized. Activation of the posteriobasal portion of the ventricles give an RS line. The normal QRS duration is approximately from 0.04 seconds to 0.12 seconds measured from the initial deflection of the QRS complex from the isoelectric line to the end of the QRS complex. The QRS complex precedes ventricular contraction.

Figure 11:
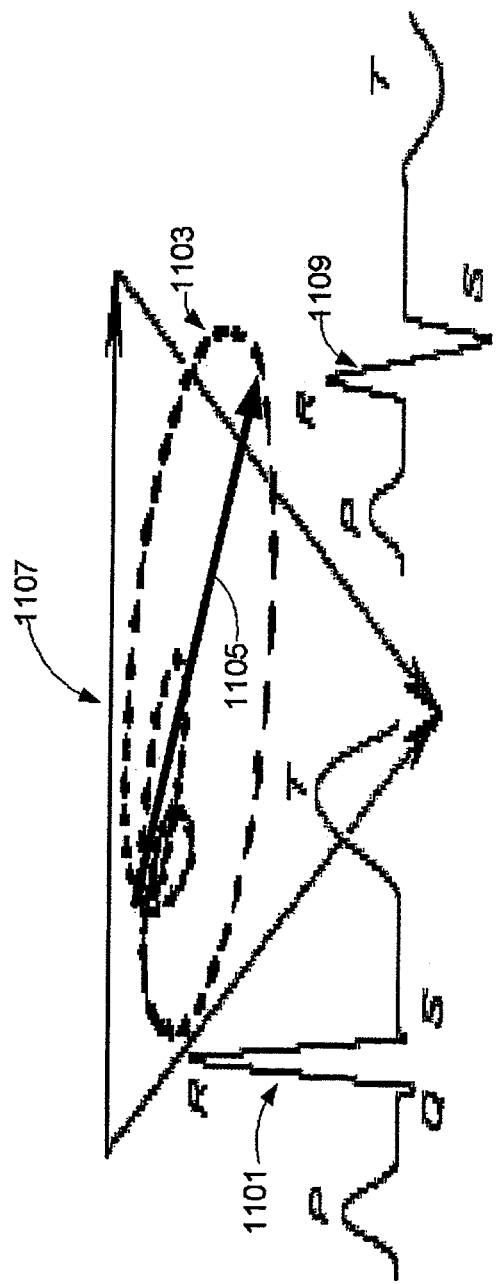
FIG. 11 shows an ECG waveform and an associated vector representation in accordance with an embodiment of the invention.

FIG. 11 shows an ECG waveform and an associated vector representation in accordance with an embodiment of the invention. FIG. 11 shows QRS complex 1101 being represented as vectors 1003 (in relation to Einthoven's triangle 1107 as will be discussed) whose trajectories also depict the magnitude and direction of the heart's impulses. The average of these vectors for a particular heart cycle is called mean QRS vector 1105 and is displayed on the vector image as a solid arrow whose length is the average magnitude and whose angle is the average direction. QRS complex 1109 corresponds to a subsequent heart cycle that can be presented by another set of vectors.

Experimental studies involving hundreds of patients compare 12-lead ECG recordings with both standard electrodes and with electrodes positioned on a diagnostic garment. The diagnostic garment may assume a garment that fits on a portion of a patient's body and may assume a form of a glove/sleeve as shown in FIGS. 2 and 3. An exemplary embodiment of the invention utilizes PhysioGlove™, which is a glove/sleeve that fits over a patient's left arm and left hand.

The standard "12 lead ECG" utilizes the three standard limb bipolar leads (lead I, lead II, and lead III), three augmented limb leads, and six precordial unipolar leads. The augmented leads are the same as the standard leads, except that the augmented leads are compared to a hypothetical null value that corresponds to a central point over the heart where no fluctuations in potential can be measured. The null point is actually mathematically determined using the electrical potentials generated by the other 2 leads. The lead on the left arm is known as an aVL lead, the lead on the right arm as an aVR lead, and the lead on the left leg as an aVF lead. Precordial leads are leads fanning across the chest. Precordial leads (V1, V2, V3, V4, V5, and V6) give more specific information about electrical conduction in the heart than the limb leads.

Figure 1:
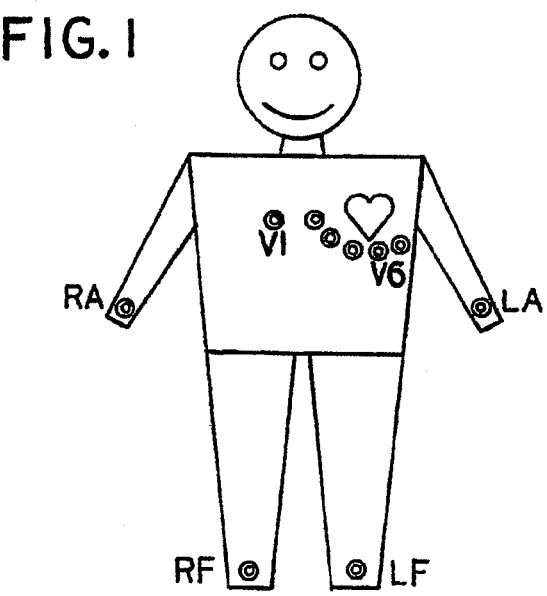
FIG. 1 depicts the classic locations for the placement of ECG electrodes on a human body for recording of a conventional 12-lead electrocardiogram.

Comparing the locations of EEG electrodes 30 on diagnostic garment 10 shown in FIG. 3 and the classic positioning of ECG electrodes as shown in FIG. 1, one observes that the locations of the corresponding EEG electrodes are different. In order to better approximate the signals from the classic positioning of ECG electrodes, the ECG signals from the EEG electrodes on diagnostic garment 10 may be compensated as will be discussed. In particular, experimental studies indicate variations in the EEG waveform are caused by positioning the LL electrode on diagnostic garment 10 rather than on the left leg.

Figure 12:
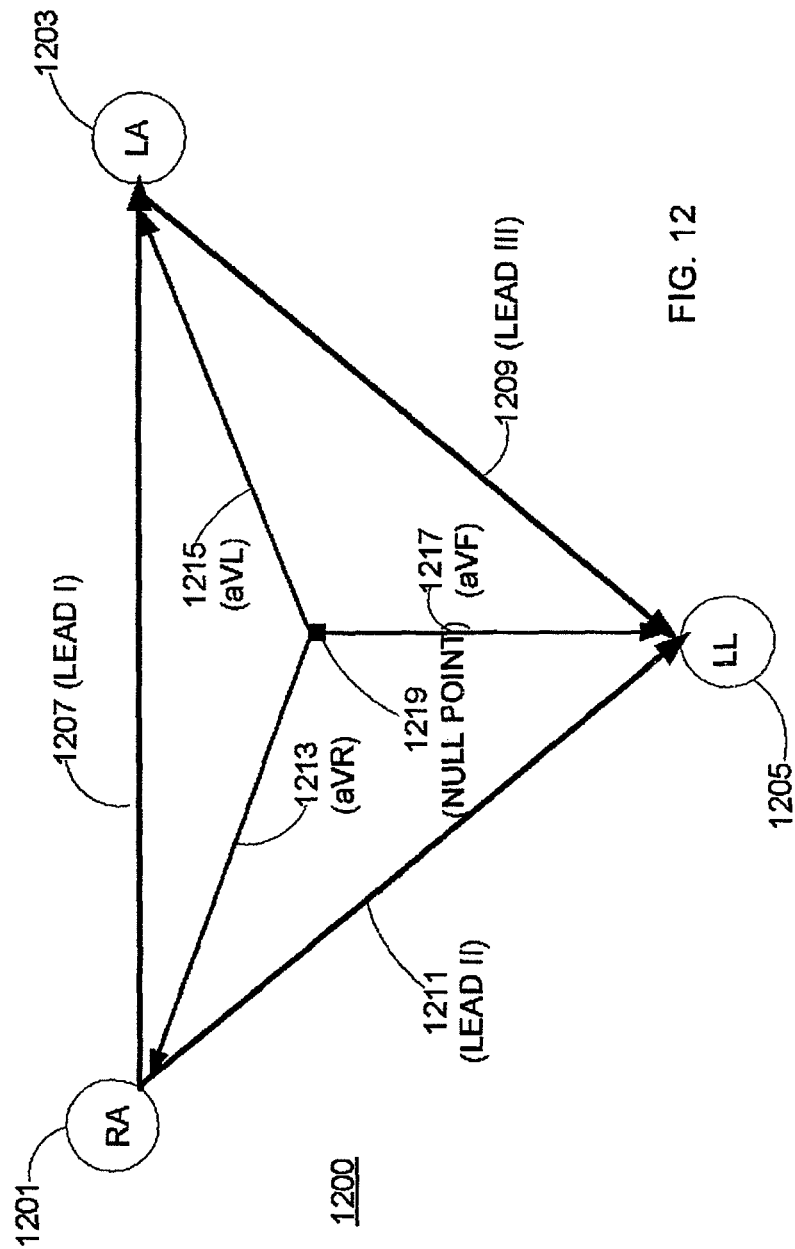
FIG. 12 shows an Einthoven's triangle representing ECG leads in accordance with an embodiment of the invention.

FIG. 12 shows an Einthoven's triangle 1200 representing (modeling) ECG leads 1207, 1209, and 1211 in accordance with an embodiment of the invention. Lead I 1207 represents the electrical potential between LA (left leg) electrode 1203 and RA (right arm) electrode 1201. Lead II 1209 represents the electrical potential between LL (left leg) electrode 1205 and LA electrode 1203. Lead III 1211 represents the electrical potential between LL electrode 1205 and RA electrode 1201. (RA electrode 1201, LA electrode 1203, and LL electrode 1205 correspond to RA, LA, and LL electrodes 30 shown in FIG. 3.) From Einthoven's triangle 1200, one can determine one lead from the other two leads by the following relationships:

$$\text{Lead } I = \text{Lead } II - \text{Lead } III \quad \text{(EQ. 1A)}$$

$$\text{Lead } II = \text{Lead } I + \text{Lead } III \quad \text{(EQ. 1B)}$$

$$\text{Lead } III = \text{Lead } II - \text{Lead } I \quad \text{(EQ. 1C)}$$

Null point 1219 is a hypothetical "null" value that exits at a central point over the heart where no fluctuations in potential can be measured. The "null point" is actually mathematically determined using the electrical potentials generated by leads 1207, 1209, and 1211. Augmented leads aVR 1213 (corresponding to the right arm), aVL 1215 (corresponding to the left arm), and aVF 1217 (corresponding to the left leg) are measured with respect to null point 1219. Augmented leads 1213, 1215, and 1217 can be expressed in terms of standard leads 1207, 1209, and 1211. For example, aVF can be expressed as:

$$aVF = 0.5 * \text{Lead } I + \text{Lead } III \quad \text{(EQ. 1D)}$$

Experimental results suggest that the mean QRS vector representing the QRS complex obtained from the patients using the diagnostic garment varies when compared with the mean QRS vector obtained from patients using standard electrodes. Experimental results also suggest that when these differences are compensated for, one can obtain an ECG waveform analogous to the one obtained using the standard electrode configuration.

Figure 13:
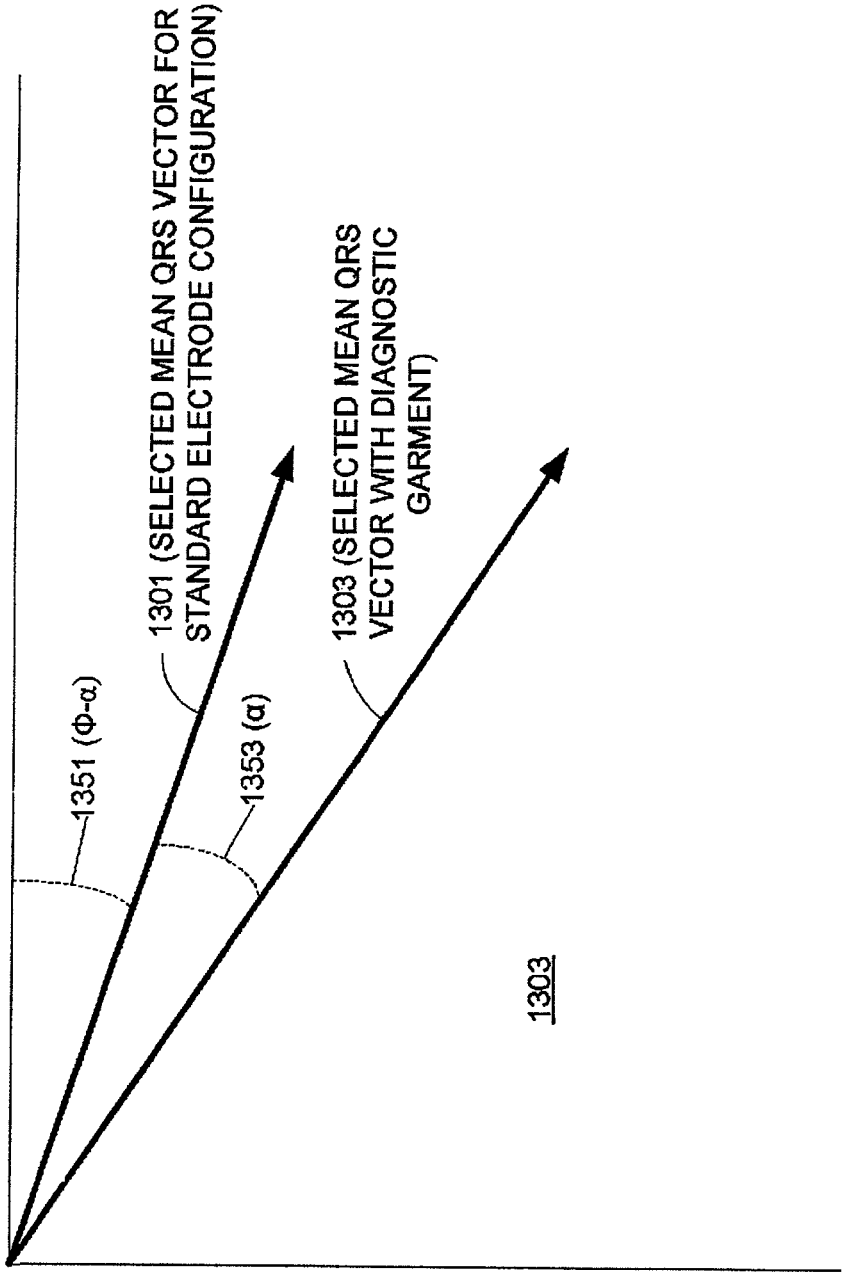
FIG. 13 shows a vector diagram for determining compensation parameters in accordance with an embodiment of the invention.

FIG. 13 shows a vector diagram 1303 for determining compensation parameters in accordance with an embodiment of the invention. Analyzing a plurality of QRS complexes, vector 1301 is the selected mean QRS vector with standard electrodes (corresponding to the ECG electrodes shown in FIG. 1) and vector 1303 is the selected mean QRS vector with electrodes positioned on the diagnostic garment (e.g., glove/sleeve 10 as shown in FIG. 2). The selection of mean QRS vectors will be discussed. Angle 1351 ($\Phi-\alpha$) and angle 1353 ($\alpha$) are used to determine a compensation factor as will be discussed.

An analysis of the mean vector of the QRS complex is made from any two of the three standard leads. In the embodiment, leads I and III are used. However, other embodiments of the invention can use lead II and lead III or lead I and lead II. The compensation process is a two-stage procedure with each stage involving a series of steps:

Stage I—Determine Compensation Parameters:

Select an ECG time interval with several QRS complexes.

Find the average vector angle for these QRS complexes. Each QRS complex is associated with a mean QRS vector (e.g., vector 1105 as shown in FIG. 11). A first plurality of mean QRS vectors is associated with the standard electrode configuration (as shown in FIG. 1) and a second plurality of mean QRS vectors is associated with the garment electrode configuration (as shown in FIG. 3).

Select the QRS complex with the angle closest to the average. A first selected mean QRS vector is selected that is closest to the average of the first plurality of mean QRS vectors and a second mean QRS vector is selected that is closest to the average of the second plurality of mean QRS vectors.

Find the compensation coefficient (k1), where $$k1 = \cos\Phi / \cos(\Phi - \alpha) \quad \text{(EQ. 2)}$$

This coefficient will be used in Stage II for performing the compensation. The angles $\Phi$ and $\Phi-\alpha$ correspond to the angles shown in FIG. 13.

Stage II—Apply the Compensating Algorithm:

The glove is a DSP device transmitting N samples per second to the receiver where N is the sample rate.

Each sample contains Lead I and Lead III voltages.

The other limb leads are combinations of these two leads.

During Stage 2, the limb lead values are compensated using the following matrix formula:

$$\begin{pmatrix} LeadI_{New} \\ LeadIII_{New} \end{pmatrix} = kA^{-1}BA \begin{pmatrix} LeadI \\ LeadIII \end{pmatrix} \quad (EQ. 3)$$

where $$\begin{pmatrix} LeadI \\ LeadIII \end{pmatrix} \text{ and } \begin{pmatrix} LeadI_{New} \\ LeadIII_{New} \end{pmatrix}$$

are the columns of lead voltages before and after the compensation, respectively. The compensation associated with Equation 3 uses the following matrix values:

$$A = \begin{pmatrix} 1 & 0 \\ 0.5 & 1 \end{pmatrix} \quad (EQ. 4)$$

$$B = \begin{pmatrix} \cos\alpha & -\sin\alpha \\ \sin\alpha & \cos\alpha \end{pmatrix} \quad (EQ. 5)$$

$$k1 = \cos\Phi / \cos(\Phi - \alpha) \quad (EQ. 6)$$

Matrix A has an inverse $$A^{-1} = \begin{pmatrix} 1 & 0 \\ -0.5 & 1 \end{pmatrix}.$$

The compensation coefficient k1 is defined in Equation 2. The determined compensation is applied to every ECG sample provided by the diagnostic garment. The compensated waveforms/reports are hence obtained.

While the exemplary embodiment selects one of the mean QRS vectors closest to an average of a plurality of mean QRS vectors, another embodiment can select a resulting mean QRS vector with another criterion. Also, another embodiment may determine a resulting mean QRS vector that corresponds to an average of the plurality of mean QRS vectors even though the resulting mean QRS vector does not correspond to actual measurement data.

The electrical signal from the heart's natural pace maker starts in what is called the SA (sinoatrial) node located in the right atrium travels through the right atrium to the ventricles (i.e. the lower chambers of the heart). The electrical signals cross a junction called the AV (atrialventricular) node going from the atruim to the ventricles. From the AV node the electrical signal travels through a path called the bundle of His that splits into two paths one on the left lower chamber and one on the right lower chamber. Each path is called a bundle branch. The electrical signals from the bundle branches causes the ventricles to contract. Normally both ventricles contract simultaneously. If one of the bundle branches is damaged then the blockage blocks or slows the electrical signal on one of the paths. The blockage of the electrical signal is called a bundle branch block. A left bundle branch block (LBBB) blocks the signal on the left side while a right bundle branch block (RBBB) blocks the signal on the right side. Patients that have a bundle branch block do not require compensation as described above. Thus, a separate algorithm may be used to detect those patients so that their ECG waveforms are not compensated.

ECG waveform noise reduction is performed in two stages, in which the signal noise results from positioning the ECG electrodes on the diagnostic garment.

Stage I—Determine the Parameter for the Compensation Filter

Select an ECG time interval with several QRS complexes.

Calculate Mod_Lead I=V6−V1 values. Electrodes V6 and V1 are positioned on the diagnostic garment as shown in FIG. 3.

Define the AVG (R(Lead I)) and AVG (R(Mod_Lead I)) for the selected time interval. R is a parameter representing the height of the QRS complex peak over the isoelectric line. R is a parameter representing the height of the QRS complex peak over the isoelectric line. In the embodiment, R corresponds to the height of the R wave 1005 as shown in FIG. 10.

Determine the compensation coefficient k2, where $$k2 = AVG(R(\text{Lead } I))/AVG(R(\text{Mod\_Lead } I)) \quad (EQ. 7)$$

The compensation coefficient k2 will be used in Stage II for performing the compensation.

Stage II—Apply the Compensating Algorithm

The glove transmits Lead I, Lead III, and V1 to V6 voltages. Lead potential VL, which is a voltage between the LL electrode and the center of Einthoven's triangle, is given by.

$$VL = LL - (LL + LA + RA)/3 \quad (EQ. 8)$$

VL voltage may also be obtained from the combination of the existing leads:

$$VL = (\text{Lead } I + 2*\text{Lead } III)/3 \quad (EQ. 9)$$

The compensated values for Lead I and Lead III are determined by:

$$\text{Lead } I_{New} = k2*(V6 - V1) \quad (EQ. 10)$$

$$\text{Lead } III_{New} = -k2*(V6 - V1)/2 + 3/2(VL) \quad (EQ. 11)$$

where Lead $I_{New}$ and Lead $III_{New}$ are values after compensation, VL is the previously defined voltage, and k2 is the compensation coefficient.

Figure 14A:
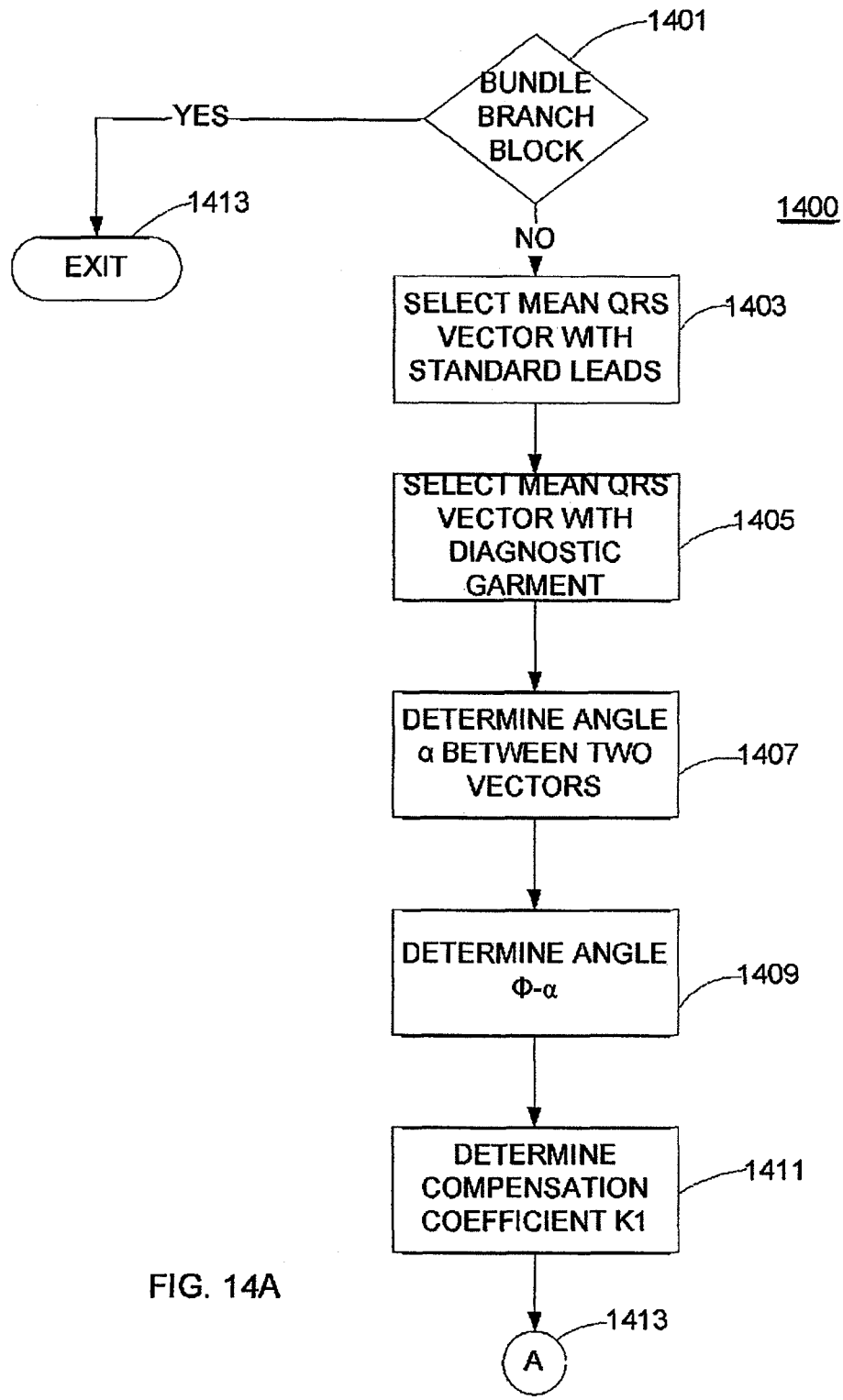
FIG. 14A shows a flow diagram for compensating for the positioning of ECG electrodes on a diagnostic garment in accordance with an embodiment of the invention.

FIG. 14A shows a flow diagram 1400 for compensating for the positioning of ECG electrodes on a diagnostic garment in accordance with an embodiment of the invention. If step 1401 determines that a patient is diagnosed with a bundle branch block (as previously discussed), then compensation of the ECG inputs is circumvented through step 1413. If not, step 1403 selects a first mean QRS vector that is closest to a first plurality of mean QRS vectors, each corresponding to a QRS complex with a standard electrode configuration. Step 1405 selects a second mean QRS vector that is closest to a second plurality of mean QRS vectors, each corresponding to a QRS complex with a garment electrode configuration. In step 1407, an angle α between the two selected mean QRS vectors is determined as shown in FIG. 13. In step 1409, an angle Φ−α between the first selected mean QRS vector and a reference axis corresponding to Lead I is determined. In step 1411, a compensation coefficient k1 (as given by EQ. 2) is determined. Procedure 1400 continues to step 1413 in order to process subsequent samples.

Figure 14B:
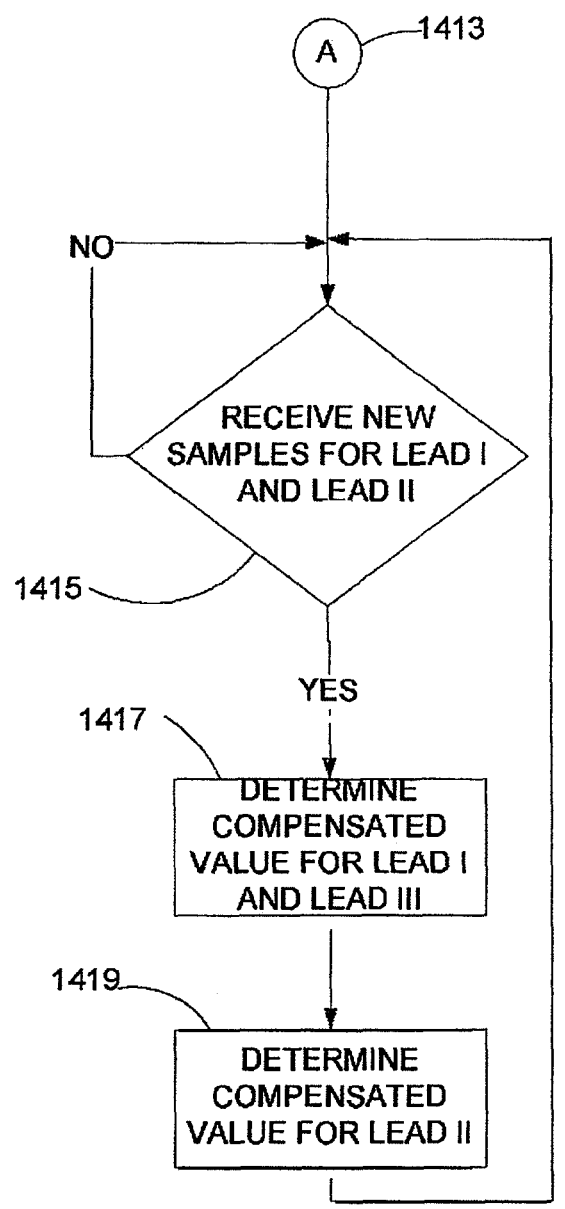
FIG. 14B shows a continuation of the flow diagram shown in FIG. 14A.

FIG. 14B shows a continuation of flow diagram 1400, in which the compensation coefficient k1 is used to compensate subsequent ECG samples obtained from the electrodes positioned on the diagnostic garment. (ECG samples are acquired every 1/N seconds, i.e., N samples per second. A sample comprises ECG measurements from a plurality of ECG electrodes as shown in FIG. 3.) Step 1415 determines if a new sample is available for Lead I (corresponding to LA 1203 minus RA 1201 as shown in FIG. 12) and for Lead III (corresponding to LL 1205 minus LA 1203 as shown in FIG. 12). If so the voltages for Lead I and Lead III are compensated using Equations 3-6 in step 1417. In Step 1419, the voltage for Lead II is determined using EQ. 1B. Steps 1415-1419 are repeated for each subsequent ECG sample.

Figure 15A:
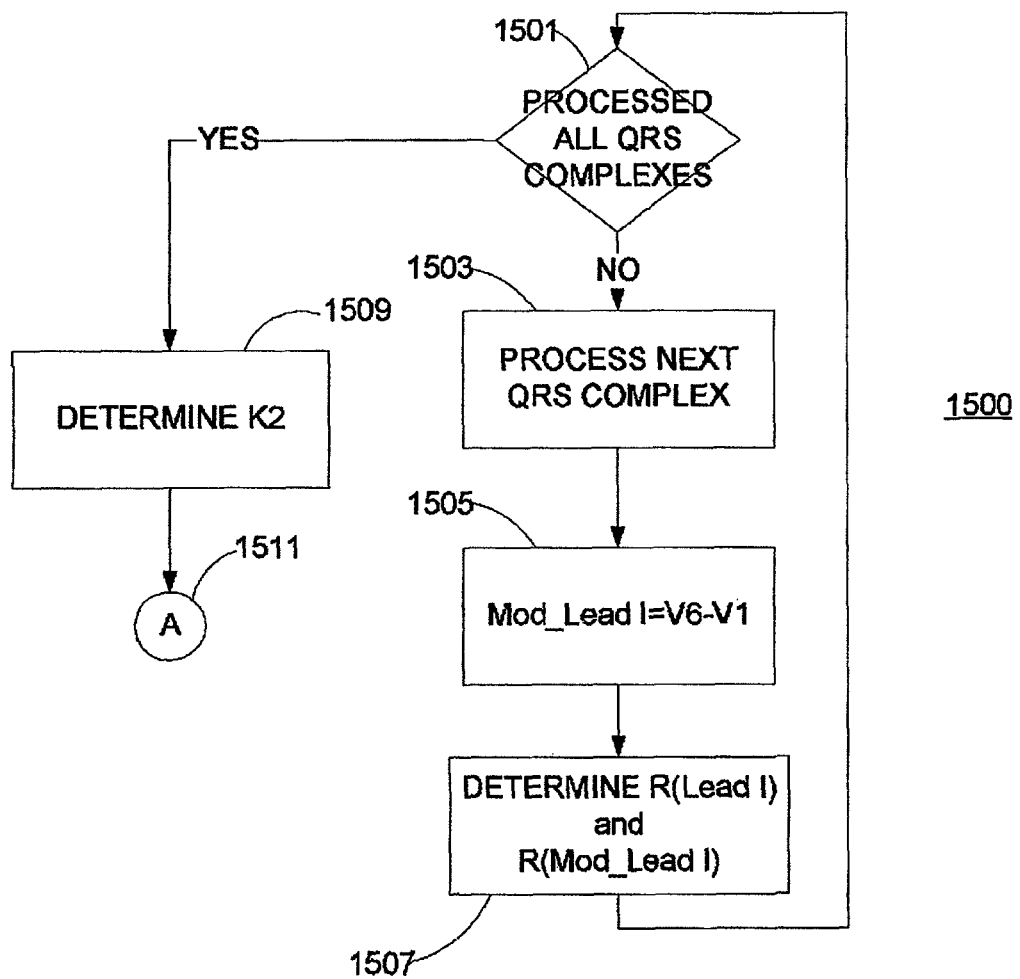
FIG. 15A shows a flow diagram for compensating for signal noise resulting from the positioning of ECG electrodes on a diagnostic garment in accordance with an embodiment of the invention.

FIG. 15A shows a flow diagram 1500 for compensating for signal noise resulting from the positioning of ECG electrodes on a diagnostic garment in accordance with an embodiment of the invention. Process 1500 determines compensation coefficient k2 in order to reduce signal noise induced by positioning ECG electrodes on the diagnostic garment, e.g., glove/sleeve 10. Step 1501 determines if all QRS complexes have been processed. If so, step 1509 determines compensation coefficient k2 using Equation 7. If not, step 1503 processes the next QRS complex.

In step 1505, a modified Lead I value is determined. With step 1507 the height of the R wave 1005 (as shown in FIG. 10) is determined for both Lead I and the modified Lead I (Mod_Lead I). Process 1500 is repeated until all QRS complexes are processed. In step 1511, once compensation coefficient k2 is determined, process 1500 continues to process subsequent ECG samples as shown in FIG. 15B.

Figure 15B:
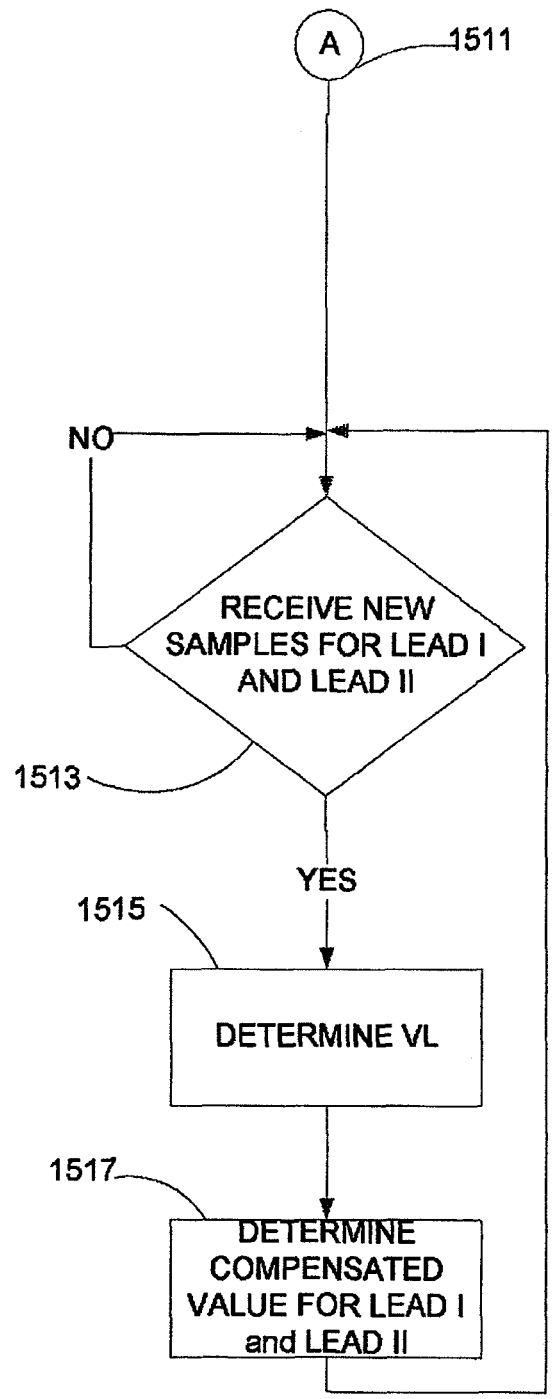
FIG. 15B shows a continuation of the flow diagram shown in FIG. 15A.

FIG. 15B shows a continuation of flow diagram 1500. If step 1513 determines that a new ECG sample is available for processing, lead potential VL is calculated with Equation 9 using Lead I and Lead III potentials in step 1515. In step 1517, compensated lead values are determined using Equations 10 and 11. Even though Equations 10 and 11 compensate for two of the three leads, the third lead can be compensated in accordance with Equations 1A-1C. Steps 1513-1517 are repeated for subsequent ECG samples.

With another embodiment of the invention, the methods shown in FIGS. 14A, 14B, 15A, and 15B can be combined so that both compensation for electrode positioning and signal noise can be performed on EEG signals received from a diagnostic garment.

The embodiments shown in FIGS. 14A, 14B, 15A, and 15B exemplify compensating ECG samples from ECG electrodes that are positioned on a diagnostic garment. However, other embodiments of the invention support other algorithms to compensate for the ECG electrodes being positioned differently from the classical locations as shown in FIG. 1. Other embodiments of the invention may position ECG electrodes at different non-classical locations and correspondingly compensate for shifts in ECG electrode positioning.

Figure 16:
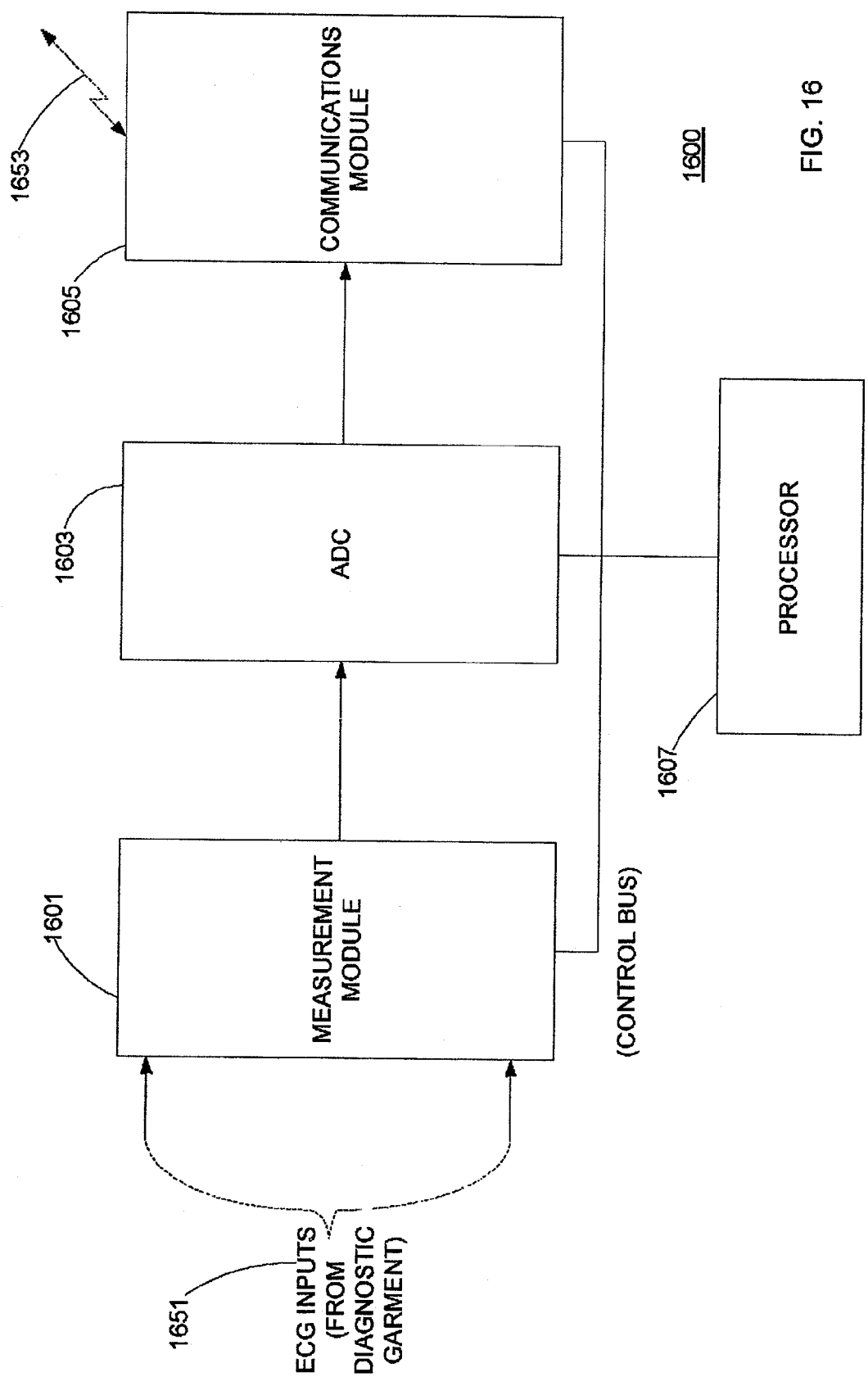
FIG. 16 shows apparatus for obtaining, transforming, and communicating ECG measurements from electrodes that are positioned on a diagnostic garment in accordance with an embodiment of the invention.

FIG. 16 shows an apparatus 1600 for obtaining, transforming, and communicating ECG measurements from electrodes that are positioned on a diagnostic garment in accordance with an embodiment of the invention. Measurement module 1601 obtains ECG inputs (samples) 1651 from ECG electrodes positioned on the diagnostic garment. In the embodiment, measurement module 1601 includes a buffer to appropriately interface to the voltage levels of the ECG electrodes and a multiplexer to interface with a plurality of ECG electrodes. Because ECG inputs typically have analog characteristics, analog to digital converter (ADC) 1603 converts analog ECG inputs into a digital format in order to process the ECG samples.

Processor 1607 may compensate the ECG samples (in accordance with processes 1400 and 1500) or may transmit the uncompensated ECG samples to a remote apparatus (e.g., apparatus 1700) over communications channel 1653 through communications module 1605. The embodiment supports different types of communications channels including wireline channels (e.g., telephone, cable and Internet channels) and wireless channels (e.g., cellular radio channels, point-to-point radio channels, and infrared point-to-point channels).

Figure 17:
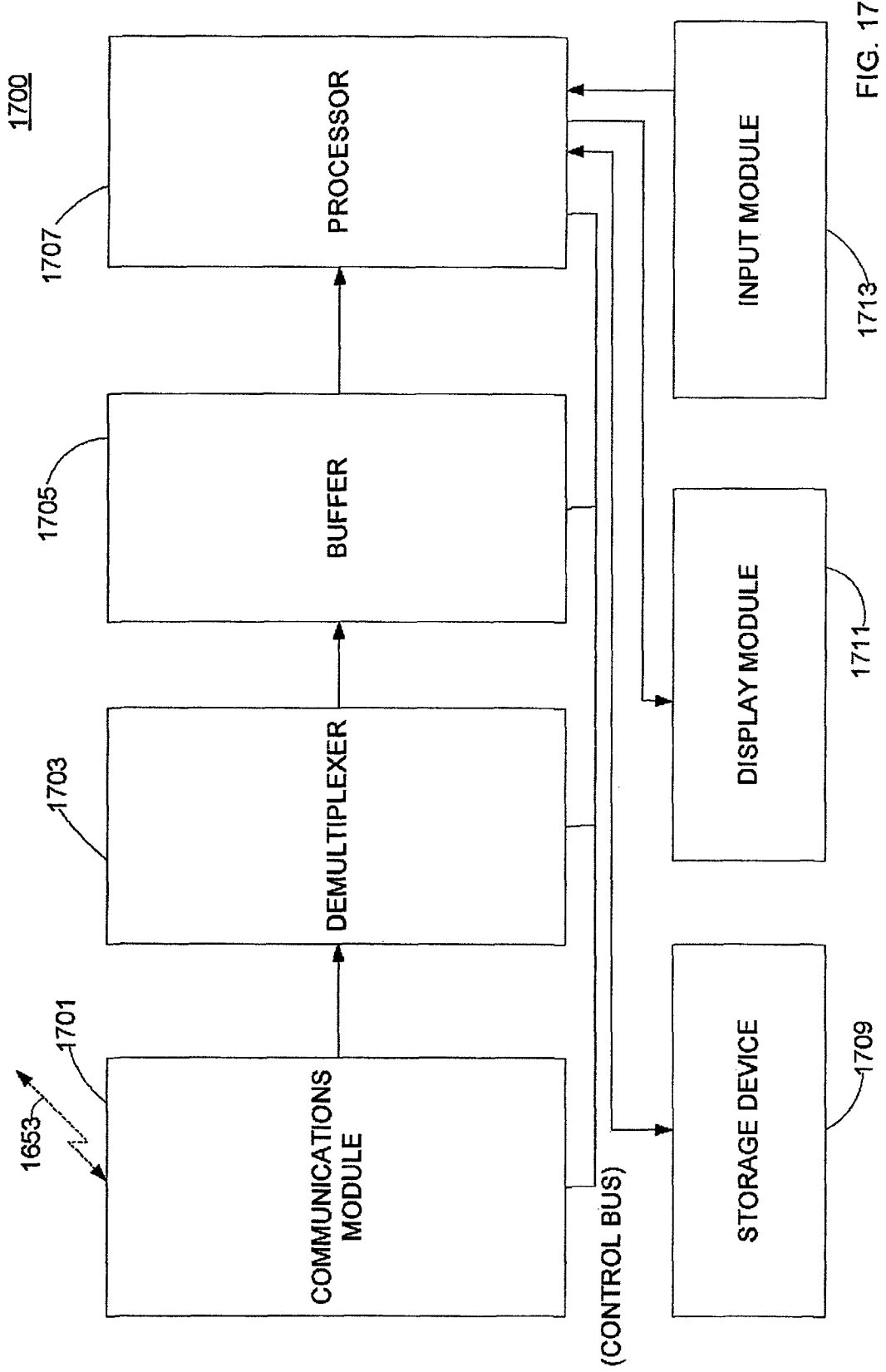
FIG. 17 shows apparatus of a remote surveillance center for receiving and processing ECG measurements in accordance with an embodiment of the invention.

FIG. 17 shows an apparatus 1700 of a remote surveillance center for receiving and processing ECG measurements in accordance with an embodiment of the invention. In the embodiment apparatus 1700 receives uncompensated samples over communications channel 1653 through communications module 1701. However, with another embodiment of the invention, apparatus 1600 may compensate ECG samples and send the compensated samples to apparatus 1700.

Apparatus 1700 receives ECG samples, in which each ECG sample comprises ECG measurements from ECG electrodes positioned on a diagnostic garment. Demultiplexer 1703 separates the ECG measurements and passes them to processor 1707 through buffer 1705. Processor 1707 processes the ECG samples. If the ECG samples are uncompensated, processor 1707 compensates the ECG samples in accordance with Equations 2-11.

The processed ECG samples may be stored in storage device 1709 for later retrieval or may be displayed on display module 1711 for a clinician to view. The clinician configures apparatus 1700 through input module 1713 for processing, storing, and displaying processed ECG samples.

As can be appreciated by one skilled in the art, a computer system with an associated computer-readable medium containing instructions for controlling the computer system can be utilized to implement the exemplary embodiments that are disclosed herein. The computer system may include at least one computer such as a microprocessor, digital signal processor, and associated peripheral electronic circuitry.

Disposable Diagnostic Garment Option

An embodiment of the invention provides a disposable version of the glove by making the glove out of a plastic material that can be inflated. By using an inflatable glove, the contour of the body (e.g., chest and torso) is automatically matched by the contour of the glove. The matching contours will allow for a close fit between the electrodes and the skin.

The inflation of the glove may be done automatically upon opening a package containing the glove by use of a one-way valve. The lower pressure within the glove will cause it to take in enough air to inflate the glove.

The electrode may be painted or printed on the plastic of the glove allowing for a low cost method of producing the glove.

The glove may be either two dimensional (i.e. a single seam) or three dimensional (i.e. multiple seams). The two dimensional reduces cost while the three dimensional version allows more flexibility in adapting the glove to the contour of the body.

Figure 18:
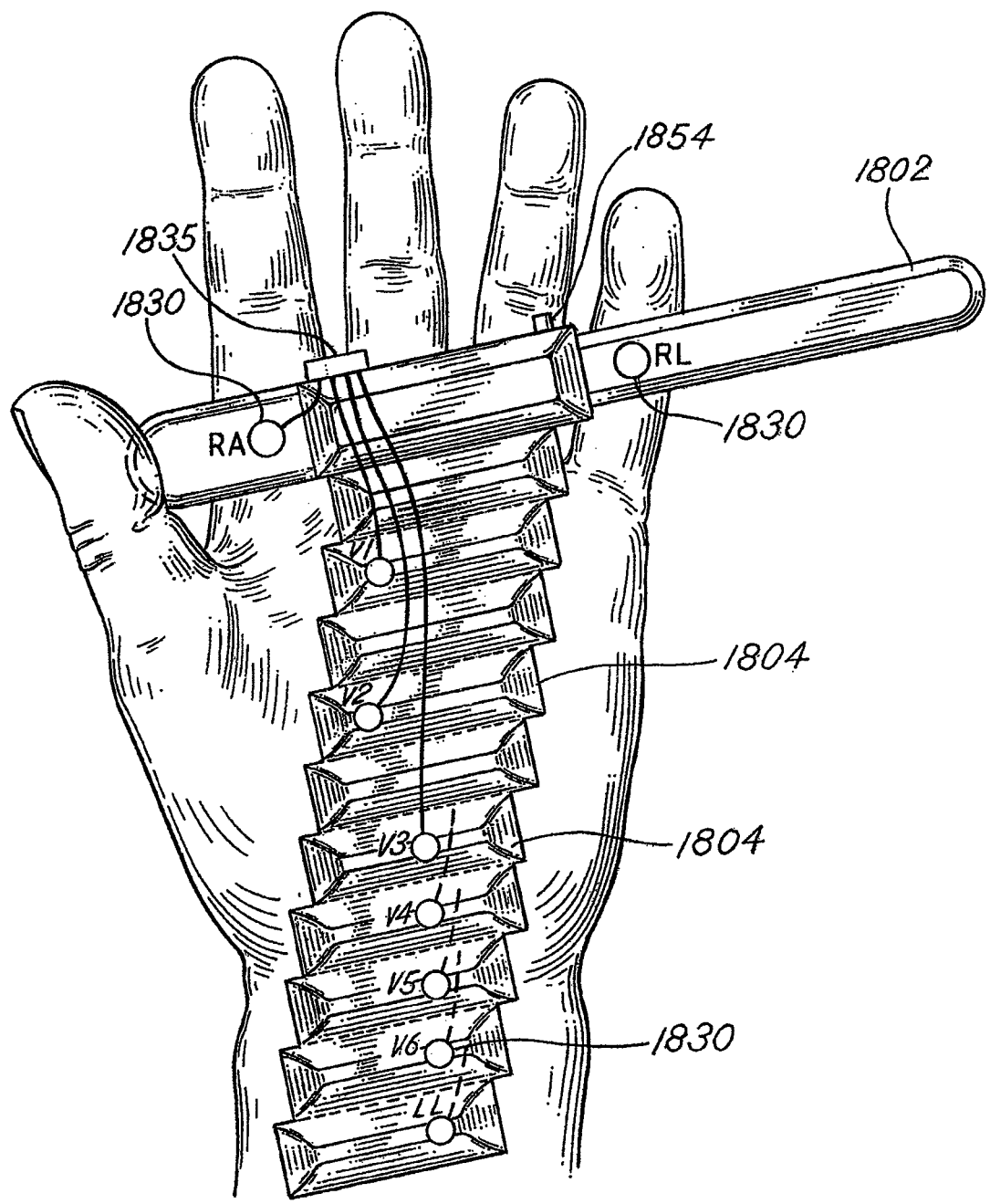
FIG. 18 is a plan view of an inflatable sensor carrying device or glove or sleeve designed to be placed upon the left hand and forearm of an individual with appropriate electrodes positioned in accord with the teachings of the invention.
Figure 19:
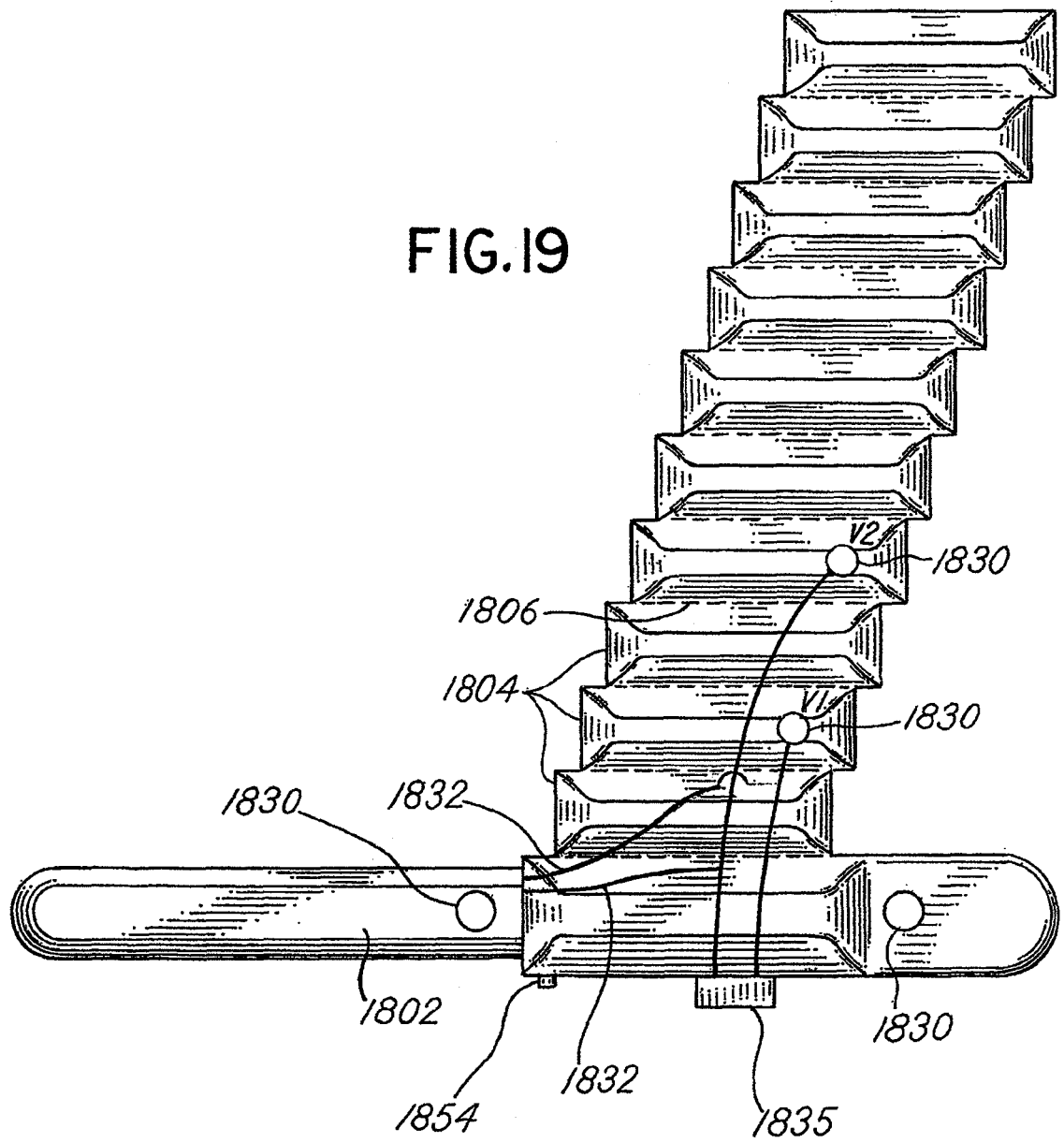
FIG. 19 is a plan view of the inflatable glove of FIG. 18 as viewed from the opposite side thereof.
Figure 20:
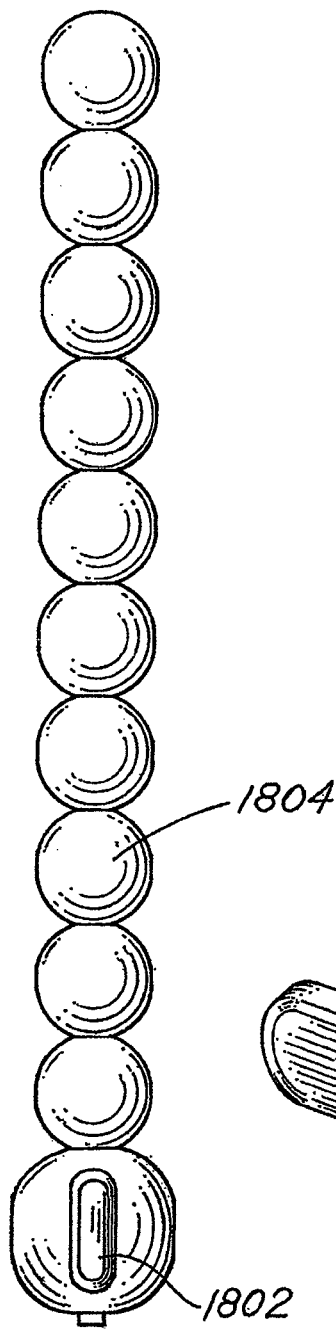
FIG. 20 is a side view of the glove of FIGS. 18 and 19.
Figure 21:
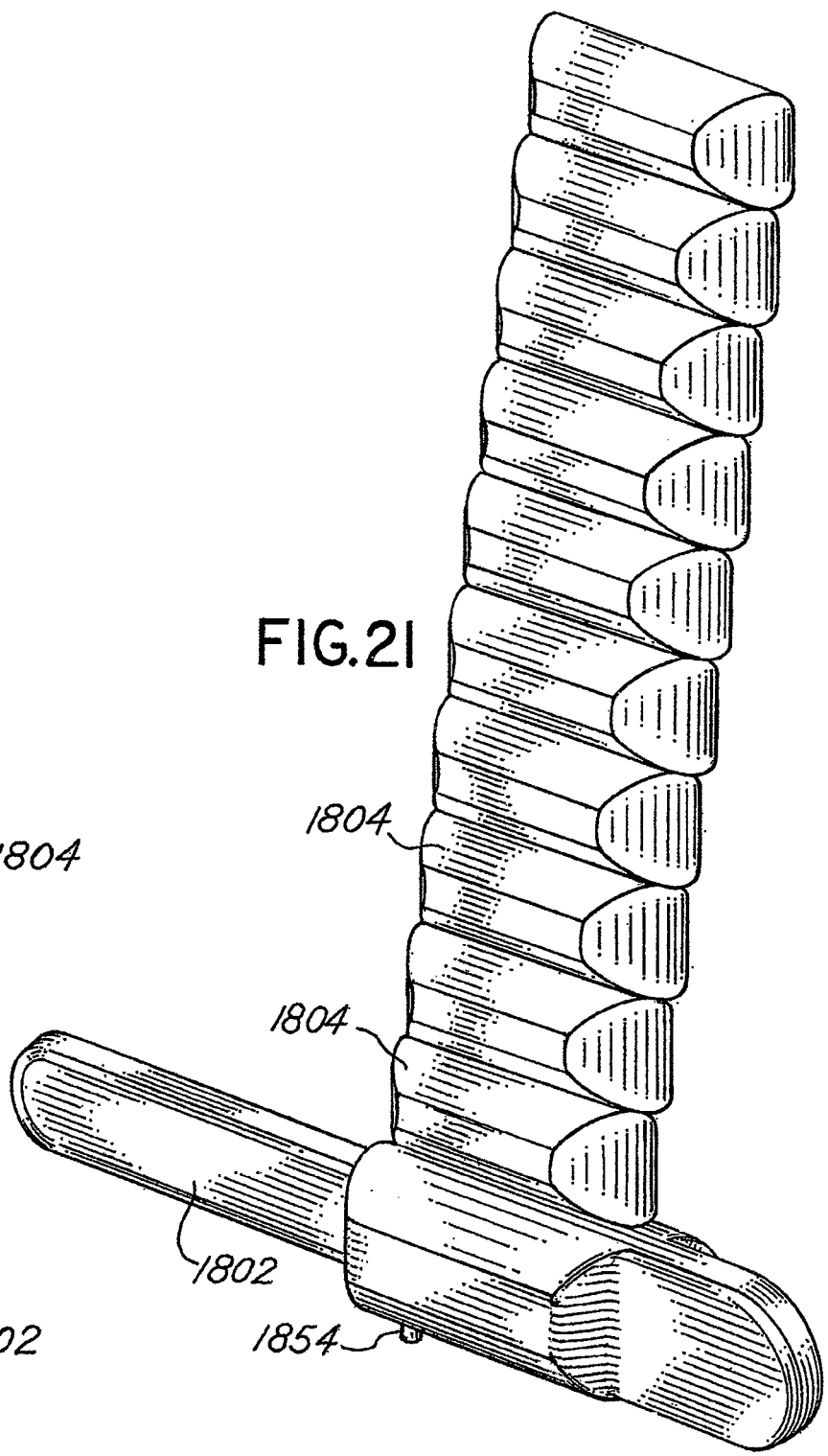
FIG. 21 is an opposite side perspective view of the glove of FIG. 18.

FIGS. 18-21 illustrate a version of an inflatable glove. The inflatable glove is in the form of a hollow rod 1802 having affixed thereto a preformed series of hollow, molded, elongate, flexible pillow members 1804. The pillow members 1804 are separated one from the other by a seam such as seam 1806 but connected by a gas flow passage. ECG electrodes such as electrodes 1830 are provided on the various inflated pillow members 1804. Electrodes 1830 are also positioned on opposite ends of the carrier rod or stick 1802. As shown in FIG. 18, the separate electrodes 1830 may include leads or lead wires 1832 connected thereto. The electrodes 1830 are spaced by virtue of their positioning on the discrete pillow members 1804 to accommodate a desired physical positioning or spacing such as would be accomplished by the sleeve and glove depicted in FIG. 3.

A valve 1834 is provided in hollow rod or tube member to effect inflation of the pillow members 1804 of the glove. The opposite side of the glove including the rod 1802 as well as the pillow members 1804, may include an appropriate adhesive for maintaining placement of the inflatable glove on the hand of an individual such as illustrated in phantom in FIG. 18.

The uninflated pillow member 1804 of the glove of the type depicted in FIG. 18 may then be folded over the rod when it is originally packaged and upon unpackaging and inflation will assume the configuration such as shown in FIGS. 18-21. The glove may then be placed upon the hand and lower arm of an individual. The glove is typically placed upon the left hand and lower arm or forearm in the manner depicted for example with respect to the glove and sleeve of FIGS. 3, 4 and 5. The pillow members 1804 may then be inflated by inserting air or a non-toxic gas through the valve mechanism 1834 into the rod 1802 and connected pillow members 1804.

The device is manufacturable in various sizes. Thus the number of pillow members or elements 1804, the length of the rod 1802, the size of the pillow elements 1804 and other dimensional characteristics of the disclosed glove may be altered in order to accommodate persons having different physiology. Additionally, the glove may be disposed following use. Further, the electrodes 1830 may be affixed to the various pillow segments 1804 by deposition of a conductive material on the inflatable plastic which is utilized to make the pillow. Likewise the leads 1832 may also be affixed by such deposition techniques and connected to a socket assembly 1835 mounted on the rod 1802. Socket assembly 1835 may then receive a plug (not shown) which connects to a central control unit 24.

Alternative aspects and features of the embodiment of FIGS. 18-21 include the capability of folding the uninflated pillow members around the rod or stick 1802. Thus the assembly can then be conveniently packaged in a small box or sealed package for subsequent removal and inflation. The pillow members 1804 may be formed of heat sealed sheets of plastic material with an air flow channel provided between the pillow member 1804. The conductive electrodes and leads may be printed on the surface of the preinflated pillow members 1804 are affixed or molded into the material forming the pillow members 1804. The pillow members 1804 may have distinct sizes and shapes. The pillow members 1804 may also be sectioned so that only discrete portions thereof inflate. The rod 1802 is typically hollow but generally rigid to facilitate manual gripping and proper positioning.

While the invention has been described with respect to specific examples including multiple modes of carrying out the invention, those skilled in the art will appreciate that there are numerous variations and permutations of the above described systems and techniques that fall within the spirit and scope of the invention as set forth in the appended claims.

What is claimed is:

1. A disposable diagnostic garment for obtaining human electrocardiogram (ECG) input readings comprising, in combination:
    a garment covering that is inflatable to automatically match a contour of a body portion of a patient, the garment covering including an arm portion for a left arm of a patient and an inside palm side; and
    at least one electrode that is affixed to the arm portion and inside palm side of the garment covering, wherein the at least one electrode is arranged on the garment covering to position the at least one electrode against the body portion of the patient and to provide a corresponding ECG signal when the garment covering is inflated and when the left arm is supported with the elbow against the body and the left forearm directed toward the right shoulder, and wherein the at least one electrode comprises RA, RL, V1, V2, V3, V4, V5, V6, LL and LA electrodes.

2. The disposable diagnostic garment of claim 1, wherein the garment covering comprises a hand portion for a left hand of the patient including wherein the at least one electrode comprises the RA, RL, V1, and V2 electrode.

3. The disposable diagnostic garment of claim 1, wherein the at least one electrode is affixed to the garment covering by depositing a conductive material on the garment covering.

4. The disposable diagnostic garment of claim 1, wherein the garment covering comprises a plastic material.

5. The disposable diagnostic garment of claim 1, further comprising:
    an inflation means for inflating the disposable diagnostic garment.

6. The disposable diagnostic garment of claim 1, further comprising:
    a one-way valve for inflating the disposable diagnostic garment.

* * * * *